US005258283A

United States Patent [19]
Frazier et al.

[11] Patent Number: 5,258,283
[45] Date of Patent: *Nov. 2, 1993

[54] DETECTION AND DIFFERENTIATION OF COXIELLA BURNETII IN BIOLOGICAL FLUIDS

[75] Inventors: Marvin E. Frazier, Richland, Wash.; Louis P. Mallavia, Moscow, Id.; James E. Samuel, Derwood, Md.; Oswald G. Baca, Albuquerque, N. Mex.

[73] Assignee: Battelle Memorial Institute, Richland, Wash.

[*] Notice: The portion of the term of this patent subsequent to Jan. 23, 2007 has been disclaimed.

[21] Appl. No.: 425,856

[22] Filed: Oct. 23, 1989

Related U.S. Application Data

[63] Continuation-in-part of Ser. No. 927,779, Nov. 5, 1986, Pat. No. 4,895,795, which is a continuation-in-part of Ser. No. 795,207, Nov. 5, 1985, Pat. No. 4,876,186.

[51] Int. Cl.$^5$ .............................. C12Q 1/68
[52] U.S. Cl. .......................... 435/6; 435/34; 435/35; 435/317.1; 436/63; 436/501; 536/24.32
[58] Field of Search .............. 435/6, 34, 35, 172.3, 435/317; 436/63, 501; 536/27; 935/29, 78

[56] References Cited

U.S. PATENT DOCUMENTS

| | | | |
|---|---|---|---|
| 4,332,898 | 6/1982 | Revusser | 435/172 |
| 4,358,535 | 11/1982 | Falkow et al. | 435/5 |
| 4,563,419 | 1/1986 | Ranki et al. | 435/6 |

FOREIGN PATENT DOCUMENTS

| | | |
|---|---|---|
| 0062237 | 3/1982 | European Pat. Off. |
| 0147665 | 11/1984 | European Pat. Off. |
| 86/05209 | 3/1986 | PCT Int'l Appl. |

OTHER PUBLICATIONS

O. G. Baca and D. Paretsky, "Q Fever and *Coxiella burnetii*: A Model for Host-Parasite Interactions," *Microbial Rev.* 47:127–49, 1983.
R. A. Ormsbee, "Q Fever Rickettsia," in *Viral and Ricketsial Infections of Man*, 45th Ed., F. L. Horsfall, Jr. and I. Tamm (ed.), J. B. Lippincott Co., PA, 1965, pp. 1144–1160.
M. G. Peacock et al., "Serological Evaluation of Q Fever in Humans: Enhanced Phase I Titers of Immunologlobulins G and A are Diagnostic for Q Fever Endocarditis," *Infec. Immun.* 41:1089–98, 1983.
W. P. G. Turck et al., "Chronic Q Fever," *Q. J. Med.* 45:193–217, 1976.
M. J. Tobin et al., "Q Fever Endocarditis," *Am. J. Med.* 72:396–400, 1982.
A. O. Robson and C. D. G. L. Shimmin, "Chronic Q Fever–I, Clinical Aspects of a Patient with Endocarditis," *Br. Med. J.* 2:980–83, 1959.
M. G. P. Stoker and P. Fiset, "Phase Variation of the Nine Mile and Other Strains of Rickettsia burnetii," *Can J. Microbiol* 2:310–21, 1956.
J. E. Samuel et al., "Isolation and Characterization of a Plasmid from Phase I *Coxiella burnetii*," *Infect. Immun.* 41:488–93, 1983.
L. P. Mallavia et al., "*Coaxiella burnetii* Plasmid DNA, in Microbiology 1984," L. Lieve and D. Schlessinger (ed)., *Amer. Soc. Microbiol.*, Washington, D.C. 1984, pp. 293–296.

(List continued on next page.)

Primary Examiner—Robert J. Hill, Jr.
Assistant Examiner—Laurie Scheiner
Attorney, Agent, or Firm—Seed and Berry

[57] ABSTRACT

Methods for detecting the presence of *Coxiella burnetii* in biological samples, as well as a method for differentiating strains of *C. burnetii* that are capable of causing acute disease from those strains capable of causing chronic disease are disclosed. The methods generally comprise treating cells contained within the biological sample to expose cellular DNA, and hybridizing the cellular DNA with a DNA probe containing DNA sequences that specifically hybridize with *C. burnetii* DNA of strains associated with the capacity to cause acute or chronic disease.

8 Claims, 36 Drawing Sheets

OTHER PUBLICATIONS

J. E. Samuel et al., "Correlation of Plasmid Type and Disease Caused by *Coxiella burnetii*," *Infect. Immun.* 49:775–79, 1985.

J. J. Leary et al., "Rapid and Sensitive Colorimetric Method for Visualizing Biotin-Labeled DNA Probes Hybridized to DNA or RNA Immobilized on Nitrocellulose: Bio-Blots," *Proc. Natl. Acad. Sci. USA* 80:4045–49, 1983.

Biological Abstract, RRM, vol. 30, 1986, (Philadelphia, U.S.) M. H. Vodkin et al., "Recognition of a causative agent of chronic endocarditis as a distinct strain of *Coxiella burnetii,*" *Genetics* 110(3, part 2):65, 1985.

Biological Abstract, RRM, vol. 29, 1985, (Philadelphia, U.S.) J. E. Samuel et al., "Transcriptional analysis of *Coxiella burnetii,*" *Abstracts of the Annual Meeting of the American Society for Microbiology,* vol. 85, No. 0, p. 67, 1985.

Biological Abstract, RRM, vol. 29, 1985, (Philadelphia, U.S.) L. P. Mallavia et al., "Grouping on *Coaxiella burnetii* isolates by restriction endonuclease analysis", *Abstracts of the Annual Meeting of the American Society for Microbiology,* vol. 85, No. 0, p. 67, 1985.

Biological Abstract, RRM, vol. 26, 1983, (Philadelphia, U.S.) J. E. Samuel et al., "Isolation and characterization of plasmid DNA from Coaxiella burnetii," *Abstracts of the Annual Meeting of the American Society for Microbiology,* vol 83, No. 0, p. 67, 1983.

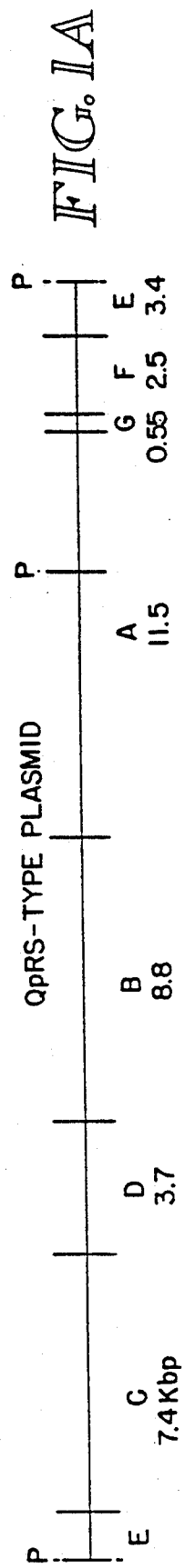
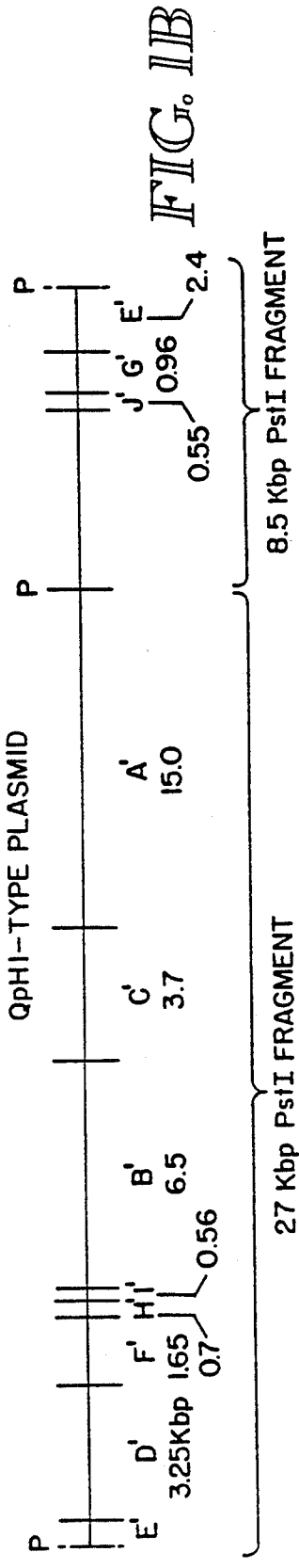

Comparison of Coxiella burnetii Plasmids

FIG. 2A QpRs - Type Plasmid 39 Kb

FIG. 2B QpH1 - Type Plasmid 36 Kb

FIG. 2C QpRS Unique Sequences

FIG. 2D Eco R1 Restriction Sites / Shared Sequences

FIG. 2E QpH1 Unique Sequences

FIG. 3

H' FRAGMENT OF QpH1-TYPE PLASMID

| | | | |
|---|---|---|---|
| 1<br>CCTTGGAAAG | 11<br>GAATGCTAGA | 21<br><u>AATTGCTATC</u> | 31<br><u>ACTGAGGGTG</u> |
| 41<br><u>ACGGCA</u>CTGC | 51<br>CATCGATCCT | 61<br>AAACAAGTGA | 71<br>TGGTCTCCAT |
| 81<br>CCACGCTCAG | 91<br>AATGAGTCTG | 101<br>TGGGAGCCGA | 111<br>TGTTACGTCG |
| 121<br>GACCTACGTC | 131<br>GGACCTACAA | 141<br>GAGCAAAAGC | 151<br>GAAAGTGAAA |
| 161<br>GTAGATGTGC | 171<br>CCCACCCTTA | 181<br>GAAAGATAGG | 191<br>ATTCAGGAAA |
| 201<br>AATTTTACAA | 211<br>ATTTATTTTC | 221<br>GATAGCTGAC | 231<br>TTCTGCGAAT |
| 241<br>ATTTTTCTTC | 251<br>TGGAGAGTTG | 261<br>TACTCAGCGA | 271<br>AGTGTATGAC |
| 281<br>GGATGCTGTC | 291<br>CAACGGAAGA | 301<br>AACAACTATT | 311<br>TGAAATTCTT |
| 321<br>TCCTCTTTGT | 331<br>AGCTCTTTGT | 341<br>ATACCGTATG | 351<br>TCCTTCTTTA |
| 361<br>GTCTTCTCAG | 371<br>AAAGCCGATT | 381<br>TTCGTTTACT | 391<br>AAATTTTCAC |
| 401<br>ATTTTTTTTC | 411<br>ACACTCGACT | 421<br>CTCAGCCATT | 431<br>GTAGGGAATC |
| 441<br>GACGGTCGAT | 451<br>GCGCCAATTT | 461<br>TTTGGTTTTT | 471<br>TACCACCTGG |
| 481<br>GCAAAGAAGT | 491<br>TTGTTTTTTT | 501<br>CAAAATAGCT | 511<br>AATGCTGCTT |
| 521<br>CTTCGTCAGT | 531<br>CATAAAGAAT | 541<br>TTCACCCC<u>AT</u> | 551<br><u>CATTTGGCTT</u> |
| 561<br><u>ATTCAAAGAA</u> | 571<br><u>CCTCA</u>GTAAA | 581<br>GACGTCGCAG | 591<br>TGTTAGGTAT |
| 601<br>GTCAGCACAT | 611<br>TGGCTGGCAG | 621<br>TCGTGCTAGA | 631<br>GTTGGTATAT |

FIG. 3 CONT.

| | | | |
|---|---|---|---|
| 641 TTGTAATTGA | 651 ATAGGATTAA | 661 ATTATTATAA | 671 TCTTTATTAT |
| 681 AATTTCAAAG | 691 TTAATATTTC | 701 GCAATTAATA | 711 AAAATGTGAA |
| 721 CGTGTCTCGG | 731 TATAATGAAC | 741 AACTTGAAAA | 751 AAAGCTTGGC |
| 761 AAATTTACGA | 771 TAGTGCTTTA | 781 TTTTATGTTA | 791 ACTATACAGC |
| 801 ACACCATTAC | 811 CGAAGTGGAG | 821 CAAAGGTGAA | 831 CTTAAGTAAT |
| 841 TTTAATTTGC | 851 CCATAGTATT | 861 AAACGCTGAG | 871 AATTC *Eco* R1 |

FIG. 4

G' FRAGMENT OF QpH1-TYPE PLASMID

```
                 1           11          21          31
5' ... G      AATTCATCAC  GTCAGGGCGA  TCTTATTATT  TTCTGTCGAA
      Eco R1

41           51          61          71
GAAGTTAAAA   TATTCAAATA  AAAAATTTAT  AACGGCTACT 81           91          101         111
AATGACAAAT   AGAATTTCTT  CATTTTGATG  CCTGATATCA 121          131         141
aGTCCTGGAC   GATCGATATT  XXXXXXXXXX  ~1160 bp..

1301         1311        1321        1331
AAATAATAGa   AAATTCATAG  ATTCGAGGAA  GAAAATAAGC 1341         1351        1361        1371        1381
GCTTAAAAAG   CGAGAATCAA  CAGCTTAAAG  ACGAACTTAA  ACTCCTCAAA 1391         1401
GCTAGGAATT   C ... 3'
      Eco R1
```

FIG. 5

A FRAGMENT OF QpRS-TYPE PLASMID

| 1 ACGACCGGAG | 11 TCTGCGCCAT | 21 CAACATCAAA | 31 GACTTTAAGA | 41 AGTAAGAATC |
|---|---|---|---|---|
| 51 CATAACTCTA | 61 TACCCACACC | 71 AGTTCGCTCC | 81 CATAAAACTA | 91 TGCCCTCAAA |
| 101 AAAACGTGGG | 111 CTGTTGTCGA | 121 TTTTTTTCTA | 131 CGGCACATAC | 141 GCTGCTTTTC |
| 151 AGGAAGGGAA | 161 TTATCTCTTC | 171 GATGACGTGT | 181 AAAAAAACCC | 191 ATTCAAAGAT |
| 201 GTGCTATCGA | 211 ACGATTAGGT | 221 CTGATCTGCG | 231 CTTACGGTGT | 241 TTTAGTCCCT |
| 251 TAGATTAACT | 261 GCTGGATTGC | 271 AGGGACTGTG | 281 TGTAACgCGA | 291 TGTAATGCGG |
| 301 CTGAAAAaGC | 311 TCGATAGAGT | 321 TTTtCcAATA | 331 GCTCACcGCc | 341 ACAGCTGGCc |
| 351 acgcactgca | 361 taatcatagc | 371 cXXXXXXXXX | XXXXXXXXX | ~8061 bp |
| 8451 XXXXXXXXXX | 8461 XXXXXXXXXX | 8471 AACGACCACT | 8481 AATCAgcAAG | 8491 GCAGTGTGCT |
| 8501 ATCAGTCTCA | 8511 GAAGGTAACC | 8521 ATGCACCGCA | 8531 GGATTGTATC | 8541 TATACACGTT |
| 8551 ATGGTTATCG | 8561 AACCCCACAG | 8571 ACCGAAACGC | 8581 CATCCGTCCT | 8591 GGGATTTAAT |
| 8601 GGGGAGCGTC | 8611 TGGACCCGGT | 8621 TAGTGGTACC *Kpn* I | 8631 TATCATTTGG | 8641 GCAATGgcTA |
| 8951 CCGCGCCTAC | 8661 AATCCGATAC | 8671 TGATGCGCTT | 8681 TAACTGCCCA | 8691 GACAGCTGGA |
| 8701 GCCCGTTTGG | 8711 TGCgGGGGAA | 8721 T<u>TAACCCTTA</u> | 8731 <u>TGCGTATTGC</u> | 8741 <u>GACGGCGATC</u> |
| 8751 CGATCAATCG | 8761 CGTGGATCCA *Bam* H1 | 8771 AATGGCCATT | 8781 TAAGTTCGCA | 8791 GGCGGAGCTC |
| 8801 GGTATTGGCT | 8811 TGGGTGTCGT | 8821 CGGCCTAGTT | 8831 TTGGCTGTCT | 8841 TTACCgCCgG |

FIG. 5 CONT.

| | | | | |
|---|---|---|---|---|
| 8851<br>CACATCCATT | 8861<br>GCGGCTGCCG | 8871<br>GTGCAATTAG | 8881<br>CGCAGCCATT | 8891<br>GAGAGTGCTT |
| 8901<br>CGGCAATCTC | 8911<br>TTTGGTGGTG | 8921<br>GGAACCCTCG | 8931<br>GCGTCGCGGC | 8941<br>GGATGTGGCA |
| 8951<br>AGCATCgCTA | 8961<br>GCGGCGCGCT | 8971<br>TGAAGATGCC | 8981<br>AATCCGCAAG | 8991<br>CGTCGGCAAC |
| 9001<br>CCTCGGATGG | 9011<br>ATCTCCCTGG | 9021<br>GATTAGGCGG | 9031<br>ACCGGGAGCC | 9041<br>GTCAGCGGCC |
| 9051<br>TGGCCACTGC<br>Pst I | 9061<br>AGCTAGAGCG | 9071<br>GgCAAAAAAT | 9081<br>TAATCTCCGG | 9091<br>GCTAGCCAAG |
| 9101<br>GGCGGCGGTA | 9111<br>AAATCAGGTC | 9121<br>ACAAAGTCCA | 9131<br>GTGTAGGGAA | 9141<br>TTAGTTATAG |
| 9151<br>AAGTCTATCT | 9161<br>AGGGGGGACC | 9171<br>cTCTtagGGG | 9181<br>AGGACCACCA | 9191<br>CACTTTAAAG |
| 9201<br>TTTGAGTAGG | 9211<br>GTTACCGTGG | 9221<br>CCCCCGAATC<br>Cla I | 9231<br>GATGCGCCCC | 9241<br>GCYGGACTCA |
| 9251<br>ATTATTGGCA | 9261<br>CAAAGTTAGT | 9271<br>CAGAAAAGCT | 9281<br>CGCTCGGGTA | 9291<br>TCAACATGTT |
| 9301<br>TTTGGGGCTG | 9311<br>ACAGAGAAAT | 9321<br>ATTTGGATAT | 9331<br>GAAATACGGG | 9341<br>AGCCTACAGA |
| 9351<br>GTTTTTCAGA | 9361<br>AGAAGACCCA | 9371<br>Gcatcacaaa | 9381<br>acgcgATATa | 9391<br>gtgattctat |
| 9401<br>cggXXXXXXX | ~4240 bp GAATTC<br>Eco R1 | | | |

FIG. 6

E FRAGMENT OF QpRS-TYPE PLASMID

| 1 | 11 | 21 | 31 | 41 |
|---|---|---|---|---|
| GAATTCAAAA<br>Eco R1 | AAAATATCT | GGCTATaATC | AATTATTTAA | CGAAAACTAG |
| 51 | 61 | 71 | 81 | 91 |
| GATAATGATT | GTCTATCGAA | GCCTAGTTTT | AACCTCTGAA | ATCCCTGTAT |
| 101 | 111 | 121 | 131 | 141 |
| GCCTAAAACT | TAAACCCGTC | ATCCCCGCTC | CCTCGTCGTC | CCCGCGCAGG |
| 151 | 161 | 171 | 181 | 191 |
| GGxacccagc | gxcactacgt | ccxxagcxxx | cgctaaaagc | xxxctggact |
| 201 | 211 | | | |
| cctgcxxxcg | ggcTCACGAA | | | |
| 221 | 231 | 241 | 251 | 261 |
| GTTTAAATGG | AAATGGCTGT | GACTTGTGGG | TAATGATGTG | GTCTTTACAT |
| 271 | 281 | 291 | 301 | 311 |
| GACACAAGTT | TTTCTAATGA | GCTTGAAGGA | GATGAGTCAT | CTAAAGACAT |
| 321 | 331 | 341 | 351 | 361 |
| GACCCCTTTT | gacgtagcaa | ttcaacttct | tttttgccaa | cagccgcttc |
| 371 | 381 | | | |
| ttgctttgcc | tgaaTTATAT | | | |
| 391 | 401 | 411 | 421 | 431 |
| TTTTGTGCTA | ATTCGGGGCA | GCATTGAGAT | CGACACGACC | TTCCTCCAGC |
| 441 | 451 | 461 | 471 | 481 |
| CACTGCCCCC | ACGTTTCAAC | GAAATCCCTC | ATATCGGATG | CTTGGTCTAC |
| 491 | 501 | 511 | 521 | 531 |
| CCCGTTTTGC | CATGCTTTCC | TCCTAACAAA | CTACTTTTA | ACTCCCAGTA |
| 541 | 551 | 561 | 571 | 581 |
| ATTAAATAGT | AGTTTATTAG | AAGCACCTGG | TCGACGTCTG | CCTTTGCCGC |
| 591 | 601 | 611 | 621 | 631 |
| TATAGTTCAC | CTTCAAATAA | ACAACAATAT | TTATTTATAA | ATTTTCGGAG |
| 641 | 651 | 661 | 671 | 681 |
| TCCATCATGC | CGCTGAGAAA | GGAAACTTTT | AAAGTAAGTT | ACACATTAGG |
| 691 | 701 | 711 | 721 | 731 |
| TTTTTTTGTG | AAAATAAATC | GACTAGCTTA | GCTTATTTAA | TCCTTTCTTA |

FIG. 6 CONT.

```
741          751          761          771          781
AAATTTTATA   ATAACGGAGA   GACTATGCCT   AAAAAACTCG   TACCCAAAGA 791          801          811          821          831
CTATGAATAT   ATCCATCTGG   ATCTTACCAC   CGGTGAAATA   AACTTTACGT 841          851          861          871          881
CGTTTAATTC   GCTTGAAGAA   TTGCAAGCCT   CTTTAAAGA    AGGTCAGATT 891          901          911          921          931
TTTTTCCACA   AAAGTGTCAT   CTTTGAAGAA   AAACCAGAAA   GTGGGGAAAT 941          951          961          971          981
TTACTCCCCT   AAACTGATAA   GCCAGATATA   TCGAAAAGAA   CAGGAACTCT 991          1001         1011         1021         1031
TTGAAATAAG   GGAAAAAAGT   AAGGGACATC   CACTACCGGT   TACTAAGAAA 1041         1051         1061         1071         1081
CTGCTTAAGA   GAGGGCAGGG   AACGATAGTG   TGTTGCGGTA   TTTACACAAA 1091         1101         1111         1121         1131
AGAACTCTTG   AAAAACGTAG   CGGAAAAGGG   ACAGTACGAT   ACCCAATGTG 1141         1151         1161         1171         1181
ACGATCTAAA   TTTGGGAATT   TTTCACGTAC   GCGCCCATAA   ACCTTTAGGC 1191         1201         1211         1221         1231
ATCGCGAAA    GGCTTGTGCA   TCTTCCGCTT   CCCGAGGATG   CTTCTTCCGC 1241         1251         1261         1271         1281
TGCAGTAGCC   ACTGAAAATT   TATTCGGCTT   AATACGATTT   ATACTCGTCA 1291         1301         1311         1321         1331
ATGATCCCGC   TAAGAAAAAA   ATTTACTTAC   CTATCTCTTG   TTTTGCAATT 1341         1351         1361         1371         1381
GAGAAGCGTA   TAGAACAAGA   GCATATAATT   GGATATTCTC   AGAAAGATAG 1391         1401         1411         1421         1431
CCTGGCGCTC   TCTCAGCGAG   CTTATTATGA   ATATAAGAAG   GACGGAACGC 1441         1451         1461         1471         1481
TTATCGGGCT   AGTCGCATTG   ATCGGTGTTG   ACGTAAAGAT   AGATGGTAAG 1491         1501         1511         1521         1531
CTAGGTTTTT   TATATCATCC   GGTGTGGCGT   GAGAAACAAT   GGGCATTAAA 1541         1551         1561         1571         1581
ATTCAATGAA   AAAATGTTTT   ATTGTGCTGT   TTCCCGTGCA   GAAAAAGAAA 1591         1601         1611         1621         1631
AAGTCTTTAA   GCCGCCTTAT   TATTTGGAGC   CGACTGCGAT   AATTGTCGAT 1641         1651         1661         1671         1681
GTAACTGAAA   CGCCCGTTAA   GCGCTTAAAG   AATACAAGTG   AGGACTATTT
```

FIG. 6 CONT.

```
1691        1701        711         1721        1731
ATGGTTGGAG  GTTTCCCAAA  TTTCGGCAAA  ATTCTCTCTT  TTTTGTGCAC 1741        1751         1761        1771        1781
AAAACAATTT  GAAATTGGAGA  AAGGCTGATT  CAAAAAATAA  ATCTCCTTTC 1791        1801        1811        1821        1831
GTGGCCCTAT  CAATGGAATC  GATTAGTGAA  TTAACAGGC   AACAGAAAAG 1841        1851        1861        1871        1881
AGCTTTTGTC  AAAATCTTGA  ATATTCCCGG  AATCATTTTC  TCTTCCTCAA 1891        1901        1911        1921        1931
CCCTAGCTAA  AGCGAGACTC  GAGAGCAAAC  TTCAATATAT  TGGACCAGCA 1941        1951        1961        1971        1981
TTAATTGAA   GCGCTGCAGA  TGGAAATTTC  ACCGATGTGG  TTGATATAAT 1991        2001        2011        2021        2031
AAATCGAATA  GAACCACTCT  ATGATTACAA  AGAGATTTTA  AAAGAGGCAT 2041        2051        2061        2071        2081
TAAAAACACA  ACGTTTGGGA  ACGGGCAATA  CTCCTTTACA  GGAGGCTATC 2091        2101        2111        2121        2131
AAAGGACAGC  ATACAGCCTA  GTTAAGTACT  TCAGTTCGCT  ATCCGCTTCG 2141        2151        2161        2171        2181
TTGAAAGTCA  TAAATCATAA  AAATCATCAA  GGATTAACAG  CACTCAATTT 2191        2201        2211        2221        2231
CGCTACAGCC  ATTGGATCAT  CCCCTGCGAT  CGTACAAGAG  CTTGAATGGT 2241        2251        2261        2271        2281
GCTCCCAATA  AAGTTAGGAA  TGGTCCGCCG  CGCAAATCAT  TGCTAATACG 2291        2301        2311        2321
TTATCTGAAA  AGGTGTCATC  CCCTTCCXXX  XXXXXXXXXX  ~980 bp 3311        3321        3331        3341        3351
XTTTGCGTCT  GATGGAAGGT  ACTGAACCAA  GTGTTGATGT  GGATATGACT 3361        3371        3381        3391        3401
CTAAAAGTC   ACCATTGAGT  CTGAGTCGGC  AAAGAGTGCC  TAGAAAAAT 3411        3421        3431        3441        3451
TAAACAATCT  GTAATGGAAT  CTGTCAAAGT  TAATCAAACT  CCTTCCCAAT 3461        3471        3481        3491        3501
CAACCTGGAT  AGCCTTGATG  ATATTTTTAT  CACTGAGTTG  CTGAACTAAG 3511        3521        3531        3541        3551
CGATGGCTTG  AAGGCCTTTT  CTATCAACGA  GGTTCAGTAA  TTTAATGAAG
```

FIG. 6 CONT.

```
3561        3571        3581        3591        3601
TGCCTCGAGG  TGTTTCTCAC  CCAACTCCCA  TTGCTTTACC  GTAGAAACAC 3611        3621        3631        3641
TGGTATTCAA  ATATTTTGCA  AAAACGGCCT  GGCTCACTTT 3651        3661
TTCATGAATT  C
   Eco R1
```

C. burnetii cells $10^8$  $10^6$  $10^4$

FIG. 8B

C. burnetii infected cells $10^6$  $10^5$  $10^4$

FIG. 8C

```
  1    GTCGACGTCTGCCTTTGCCGCTATAGTTCACCTTCAAATAAACAACAATATTTATTTATA    60

61    AATTTTCGGAGTCCATCATGCCGCTGAGAAAGGAAACTTTTAAAGTAAGTTACACATTAG   120

-35                     -10
121    GTTTTTTTGTGAAAATAAATCGACTAGCTTAGCTTATTTAATCCTTTCTTAAAATTTTAT   180 oooooooo
181    AATAACGGAGAGACTATGCCTAAAAAACTCGTACCCAAAGACTATGAATATATCCATCTG   240
                     MetProLysLysLeuValProLysAspTyrGluTyrIleHisLeu 241    GATCTTACCACCGGTGAAATAAACTTTACGTCGTTTAATTCGCTTGAAGAATTGCAAGCC   300
       AspLeuThrThrGlyGluIleAsnPheThrSerPheAsnSerLeuGluGluLeuGlnAla 301    TCTTTAAAAGAAGGTCAGATTTTTTTCCACAAAAGTGTCATCTTTGAAGAAAAACCAGAA   360
       SerLeuLysGluGlyGlnIlePhePheHisLysSerValIlePheGluGluLysProGlu 361    AGTGGGGAAATTTACTCCCCTAAACTGATAAGCCAGATATATCGAAAAGAACAGGAACTC   420
       SerGlyGluIleTyrSerProLysLeuIleSerGlnIleTyrArgLysGluGlnGluLeu 421    TTTGAAATAAGGGAAAAAAGTAAGGGACATCCACTACCGGTTACTAAGAAACTGCTTAAG   480
       PheGluIleArgGluLysSerLysGlyHisProLeuProValThrLysLysLeuLeuLys 481    AGAGGGCAGGGAACGATAGTGTGTTGCGGTATTTACACAAAAGAACTCTTGAAAAACGTA   540
       ArgGlyGlnGlyThrIleValCysCysGlyIleTyrThrLysGluLeuLeuLysAsnVal 541    GCGGAAAAGGGACAGTACGATACCCAATGTGACGATCTAAATTTGGGAATTTTTCACGTA   600
       AlaGluLysGlyGlnTyrAspThrGlnCysAspAspLeuAsnLeuGlyIlePheHisVal 601    CGCGCCCATAAACCTTTAGGCATCGCGCAAAGGCTTGTGCATCTTCCGCTTCCCGAGGAT   660
       ArgAlaHisLysProLeuGlyIleAlaGlnArgLeuValHisLeuProLeuProGluAsp 661    GCTTCTTCCGCTGCAGTAGCCACTGAAAATTTATTCGGCTTAATACGATTTATACTCGTC   720
       AlaSerSerAlaAlaValAlaThrGluAsnLeuPheGlyLeuIleArgPheIleLeuVal 721    AATGATCCCGCTAAGAAAAAAATTTACTTACCTATCTCTTGTTTTGCAATTGAGAAGCGT   780
       AsnAspProAlaLysLysLysIleTyrLeuProIleSerCysPheAlaIleGluLysArg 781    ATAGAACAAGAGCATATAATTGGATATTCTCAGAAAGATAGCCTGGCGCTCTCTCAGCGA   840
       IleGluGlnGluHisIleIleGlyTyrSerGlnLysAspSerLeuAlaLeuSerGlnArg 841    GCTTATTATGAATATAAGAAGGACGGAACGCTTATCGGGCTAGTCGCATTGATCGGTGTT   900
       AlaTyrTyrGluTyrLysLysAspGlyThrLeuIleGlyLeuValAlaLeuIleGlyVal 901    GACGTAAAGATAGATGGTAAGCTAGGTTTTTTATATCATCCGGTGTGGCGTGAGAAACAA   960
       AspValLysIleAspGlyLysLeuGlyPheLeuTyrHisProValTrpArgGluLysGln
```

*FIG. 19*

```
961   TGGGCATTAAAATTCAATGAAAAAATGTTTTATTGTGCTGTTTCCCGTGCAGAAAAAGAA   1020
      TrpAlaLeuLysPheAsnGluLysMetPheTyrCysAlaValSerArgAlaGluLysGlu

1021  AAAGTCTTTAAGCCGCCTTATTATTTGGAGCCGACTGCGATAATTGTCGATGTAACTGAA   1080
      LysValPheLysProProTyrTyrLeuGluProThrAlaIleIleValAspValThrGlu

1081  ACGCCCGTTAAGCGCTTAAAGAATACAAGTGAGGACTATTTATGGTTGGAGGTTTCCCAA   1140
      ThrProValLysArgLeuLysAsnThrSerGluAspTyrLeuTrpLeuGluValSerGln

1141  ATTTCGGCAAAATTCTCTCTTTTTTGTGCACAAAACAATTTGAAATTGGAGAAGGCTGAT   1200
      IleSerAlaLysPheSerLeuPheCysAlaGlnAsnAsnLeuLysLeuGluLysAlaAsp

1201  TCAAAAAATAAATCTCCTTTCGTGGCCCTATCAATGGAATCGATTAGTGAATTAACAGGC   1260
      SerLysAsnLysSerProPheValAlaLeuSerMetGluSerIleSerGluLeuThrGly

1261  GAACAGAAAAGAGCTTTTGTCAAAATCTTGAATATTCCCGGAATCATTTTCTCTTCCTCA   1320
      GluGlnLysArgAlaPheValLysIleLeuAsnIleProGlyIleIlePheSerSerSer

1321  ACCCTAGCTAAAGCGAGACTAGAGAGCAAACTTCAATATATTGGACCAGCATTAATTGAA   1380
      ThrLeuAlaLysAlaArgLeuGluSerLysLeuGlnTyrIleGlyProAlaLeuIleGlu

1381  GCCGCTGCAGATGGAAATTTCACCGATGTGGTTGATATAATAAATCGAATAGAACCACTC   1440
      AlaAlaAlaAspGlyAsnPheThrAspValValAspIleIleAsnArgIleGluProLeu

1441  TATGATTACAAAGAGATTTTAAAAGAGGCATTAAAAACACAACGTTTGGGAACGGGCAAT   1500
      TyrAspTyrLysGluIleLeuLysGluAlaLeuLysThrGlnArgLeuGlyThrGlyAsn

1501  ACTCCTTTACAGGAGGCTATCAAAGGACAGCATACAAGCCTAGTTAAGTACTTCAGTTCG   1560
      ThrProLeuGlnGluAlaIleLysGlyGlnHisThrSerLeuValLysTyrPheSerSer

1561  CTATCCGCTTCGTTGAAAGTCATAAATCATAAAAATCATCAAGGATTAACAGCACTCAAT   1620
      LeuSerAlaSerLeuLysValIleAsnHisLysAsnHisGlnGlyLeuThrAlaLeuAsn

1621  TTCGCTACAGCCATTGGATCATCCCCTGCGATCGTACAAGAGCTTGAATGGTGCTCCCAA   1680
      PheAlaThrAlaIleGlySerSerProAlaIleValGlnGluLeuGluTrpCysSerGln

1681  TAAAGTTAGGAATGGTCCGCCGCGCAAATCATTGCTAATACGTTATCTGAAAAGGTGTCA   1740

1741  TCCCCTTCC   1749
```

*FIG. 19 CONT.*

PROBE: pUC19/E_PST

TOTAL DNA ON FILTER

|  | QpH1/pHK17 | "S" | pUC19/E_PST | | NINE MILE | PRISCILLA | |
|---|---|---|---|---|---|---|---|
| | 1000ng | 1000 | 100 | | 1000ng | 1000 | |
| | 100 | 100 | 10 | | 100 | 100 | |
| | 10 | 10 | | | 10 | 10 | |
| | 1 | | | | 1 | 1 | |
| | | | | | | 0.1 | |
| | | | | | | 0.01 | |

FIG. 22

C. BURNETII PROBE PREPARATION-DISEASE SPECIFIC

- GENOME
- PLASMIID
  - UNIQUE DNA REGIONS
    - CLONED DNA FRAGMENTS
      - DNA SEQUENCES DETERMINED
        - OLIGONUCLEOTIDE PROBES
        - PRIMERS FOR PCR (DNA AMPLIFICATION)
          - IDENTIFICATION OF AMPLIFIED DNA FRAGMENT
            - DETERMINE DNA SEQUENCE
            - SIZE DNA IN GEL
            - HYBRIDIZATION
          - PREPARATION OF DNA PROBE
            - USE AS PROBE IN HYBRIDIZATIONS
            - CLONE AND USE AS PROBE
      - USED AS PROBE IN HYBRIDIZATIONS

*FIG. 27*

DETECTION AND DIFFERENTIATION OF COXIELLA BURNETII IN BIOLOGICAL FLUIDS

CROSS-REFERENCE TO RELATED APPLICATION

This application is a continuation-in-part of co-pending application Ser. No. 927,779, filed Nov. 5, 1986, now U.S. Pat. No. 4,895,795; which is a continuation-in-part of co-pending application Ser. No. 795,207, filed Nov. 5, 1985, now U.S. Pat. No. 4,876,186.

TECHNICAL FIELD

The present invention relates to a method for detecting *Coxiella burnetii* infection in humans and animals, and to a method for differentiating *C. burnetii* strains which cause acute disease (e.g., fever, pneumonia or other flu-like symptoms) from those capable of causing chronic disease (e.g., endocarditis, hepatitis or late-term abortions).

BACKGROUND OF THE INVENTION

*Coxiella burnetii* is an obligate intracellular parasite which is generally transmitted from animals to humans. Domestic livestock serve as a reservoir for *C. burnetii* in most parts of the world, and the disease usually presents as an unapparent infection; in sheep, however, it may lead to late-term abortion. In domestic animals (e.g., sheep, goats and cattle) the disease is shed in urine, feces and placentas, and transmitted either by aerosol or through an intermediate vector (e.g., tick). Further, apparently healthy animals may contain enormous numbers of parasites in placental tissues (Luoto & Huebner, *Public Health Rep.* 65:541-544, 1950).

Although *C. burnetii* may be transmitted to humans by ticks, it is usually contracted by inhalation of contaminated dusts and aerosols; contagion between humans is rare. *C. burnetii* is known to infect many species of animals and birds (Babudieri, *Adv. Vet. Sci.* 5:81-154, 1959). *C. burnetii* infection is most common among slaughterhouse employees and farm workers who handle domestic animals or animal products (e.g., wool or hides) (Ormsbee, *Ann. Rev. Microbiol.* 23:275-292, 1962; Baca & Paretsky, *Microbiol. Rev.* 47:127-149, 1983).

The acute disease caused by *C. burnetii* is rarely fatal to humans. The death rate has been estimated at less than 1% among Caucasians, and somewhat higher among indigenous people of equatorial Africa (Ormsbee, *Viral and Rickettsial Infections of Man*; 4th Ed., ed. F.L. Horsfall Jr. and I. Tamm, pp. 1144-1160, 1985, J. B. Lippincott, Co., Pa.). The incubation period ranges from 1 to 3 weeks, and the disease normally presents as an acute febrile illness. Recovery generally occurs within 1 to 4 weeks, depending on the course of treatment. Occasionally, *C. burnetii* infection is manifested in other ways, including apparent persistent infection, which can lead to endocarditis or other symptoms in man. The development of chronic endocarditis in humans has previously been thought to arise when a *C. burnetii* infection is superimposed on a preexisting disease or deformity of the patient, rather than being attributed to a specific property of the pathogen (Peacock et al., *Infect. & Immun.* 41:1089-1098, 1983; Turck et al., *J. Medicine* 178:193-217, 1976; Tobin et al., *Amer. J. Med.* 72:396-399, 1982; Robson et al., *British Med. J.* 2:980-983, 1959). Comparative analyses of infected sera and of the biological properties of microorganisms isolated from various sequelae of *C. burnetii* infection (acute disease, chronic endocarditis, abortion, etc.) have not indicated that specific *C. burnetii* variants produce a particular manifestation. Comparative analyses have, however, demonstrated antigenic variation in *C. burnetii* (Stoker & Fiset, *Can. J. Microbiol.* 2:310-321, 1956). This antigenic phase variation is characterized primarily by the reactivity of different isolates with hyperimmune sera against a phase I or phase II Nine Mile strain of *C. burnetii*. However, this phenotypic variation cannot be used to predict sequelae of *C. burnetii* infection.

Differentiation of *C. burnetii* caused symptoms from influenza, primary atypical pneumonia, bacterial pneumonia, or a number of other types of pneumonia and flu-like symptoms caused by a variety of etiological agents is a slow and difficult process. It is also difficult to differentiate *C. burnetii*-induced hepatitis from infectious or idiopathic hepatitis. Present differentiation procedures require isolation of *C. burnetii* from tissues or blood, and subsequent culture in embryonated eggs or in guinea pigs. An alternative method for differentiation requires demonstration of a significant rise in specific anti-*C. burnetii* antibody titer in successive serum samples. Isolation of *C. burnetii* is highly hazardous, and is inadvisable in the absence of adequate (P-3) isolation facilities. Even then, safety procedures must be rigidly followed to avoid contamination. In addition, confirmation of findings usually takes 2 to 3 weeks. Serological methods, while simpler and safer than culturing, also require considerable time (usually 3 weeks) to confirm the diagnosis, and are therefore of little use to a practicing physician, who usually prefers to start treatment within 24 hours. In addition to being costly and time-consuming, both techniques require highly specialized facilities, equipment, and reagents that are generally available only in special laboratories. Furthermore, serological diagnosis of chronic *C. burnetii* infections would be difficult since the appropriate (pre-immune) serum sample necessary for a definitive diagnosis would not be available.

Due to these difficulties in diagnosis, it is hard to accurately estimate the prevalence of *C. burnetii* infection throughout the world. Furthermore, there has been no way to predict from the initial symptoms the result of the infection, i.e., whether it will result in a persistent infection, including hepatitis and/or chronic endocarditis, or in acute disease symptoms. Such differential diagnosis is important for a number of reasons. For example, the prognosis for infections caused by acute disease strains is quite good. While debilitating symptoms may result if left untreated, appropriate treatment (with tetracyclines, for example) results in a rapid cure of the malady. However, it is important to specifically diagnose acute disease caused by *C. burnetii* infections because tetracycline is not the antibiotic of choice for treatment of most acute disease symptoms, such as pneumonias, fevers or other flu-like symptoms. It is also important to diagnose disease caused by chronic strains of *C. burnetii* due to the risk of developing complications that are usually fatal. There is currently no known cure for these chronic infections. Finally, it is important to be able to determine which animals harbor *C. burnetii* and to be able to determine if certain species, or herds, are serving as natural reservoirs for chronic disease-causing strains which may infect humans.

Accordingly, there exists a need in the art for a rapid, sensitive, and simple method for the detection of *C.*

*burnetii* in biological samples. In addition, a method for distinguishing *C. burnetii* strains capable of causing chronic disease from those associated only with acute infection would be useful for determining optimal patient treatment. The present invention fulfills these needs and further provides other related advantages.

Disclosure of the Invention

Briefly stated, the present invention provides methods for detecting the presence of *Coxiella burnetii* in biological samples. The methods generally comprise treating cells contained within the biological sample to expose cellular DNA; hybridizing the cellular DNA with a *C. burnetii*-specific labeled DNA probe; and detecting the hybridized, labeled DNA probe. It is also preferable to first immobilize the cells contained within the biological sample onto a solid support. For purposes of the present invention, the term "cellular DNA" is defined to include any and all DNA present within the cell, including the DNA of any infectious agent, such as rickettsial DNA, to which the probes will hybridize. A variety of biological samples are suitable for use within the methods described herein, including samples of blood, urine, milk, sputum or tissue.

A related aspect of the present invention provides a method for detecting the presence of strains of *C. burnetii* that are capable of causing chronic disease, comprising: treating cells contained within a biological sample to expose cellular DNA; hybridizing the cellular DNA with a labeled DNA probe containing DNA sequences that specifically recognize *C. burnetii* DNA of strains associated with the capacity to cause chronic disease; and detecting the hybridized, labeled DNA probe and therefrom determining the presence of strains of *C. burnetii* capable of causing chronic disease.

A third aspect of the present invention provides a method for differentiating strains of *C. burnetii* that are capable of causing acute disease from those capable of causing chronic disease, comprising: treating cells suspected of containing *C. burnetii* to expose cellular DNA; hybridizing a portion of the cellular DNA with a *C. burnetii*-specific labeled DNA probe; hybridizing another portion of the cellular DNA with a labeled DNA probe containing DNA sequences that specifically recognize *C. burnetii* DNA of strains associated with the capacity to cause chronic disease; and detecting the hybridized, labeled DNA probes, and therefrom differentiating the strain of *C. burnetii*.

Another aspect of the present invention discloses a method for detecting and/or differentiating strains of *C. burnetii* by employing the polymerase chain reaction (PCR), and requires knowledge of specific DNA sequences in the target region.

Still another aspect of the present invention discloses a method for classifying the genomic grouping of *C. burnetii* isolates and the use of such isolates in the detection and/or differentiation of *C. burnetii* stains capable of causing acute or chronic disease.

These and other aspects of the invention will become apparent upon reference to the following detailed description and attached drawings.

BRIEF DESCRIPTION OF THE DRAWINGS

FIGS. 1A, 1B and 1C depict a comparison of Eco RI restriction fragments of *C. burnetii* plasmid types QpH1 and QpRS.

FIGS. 2A, 2B, 2C, 2D and 2E illustrate shared and unique sequences of QpRS-type and QpH1-type plasmids.

FIG. 3 is a partial sequence map of the H' fragment of a QpH1-type plasmid.

FIG. 4 is a partial sequence map of the G' fragment of a QpH1-type plasmid.

FIG. 5 is a partial sequence map of the A fragment of a QpRS-type plasmid.

FIG. 6 is a partial sequence map of the E fragment of a QpRS-type plasmid.

FIGS. 8a, 8b and 8c illustrate the detection of *C. burnetii* in various samples.

FIG. 19 depicts the nucleotide sequence of the sense strand (5' to 3'), and deduced amino acid sequence of the *C. burnetii* cbE gene.

FIG. 22 illustrates the detection of chronic strains of *C. burnetii*.

FIG. 27 illustrates a variety of techniques which may be utilized in the practice of the present invention once it is determined that a *C. burnetii* strain contains unique DNA regions.

BEST MODE FOR CARRYING OUT THE INVENTION

Figure 7:
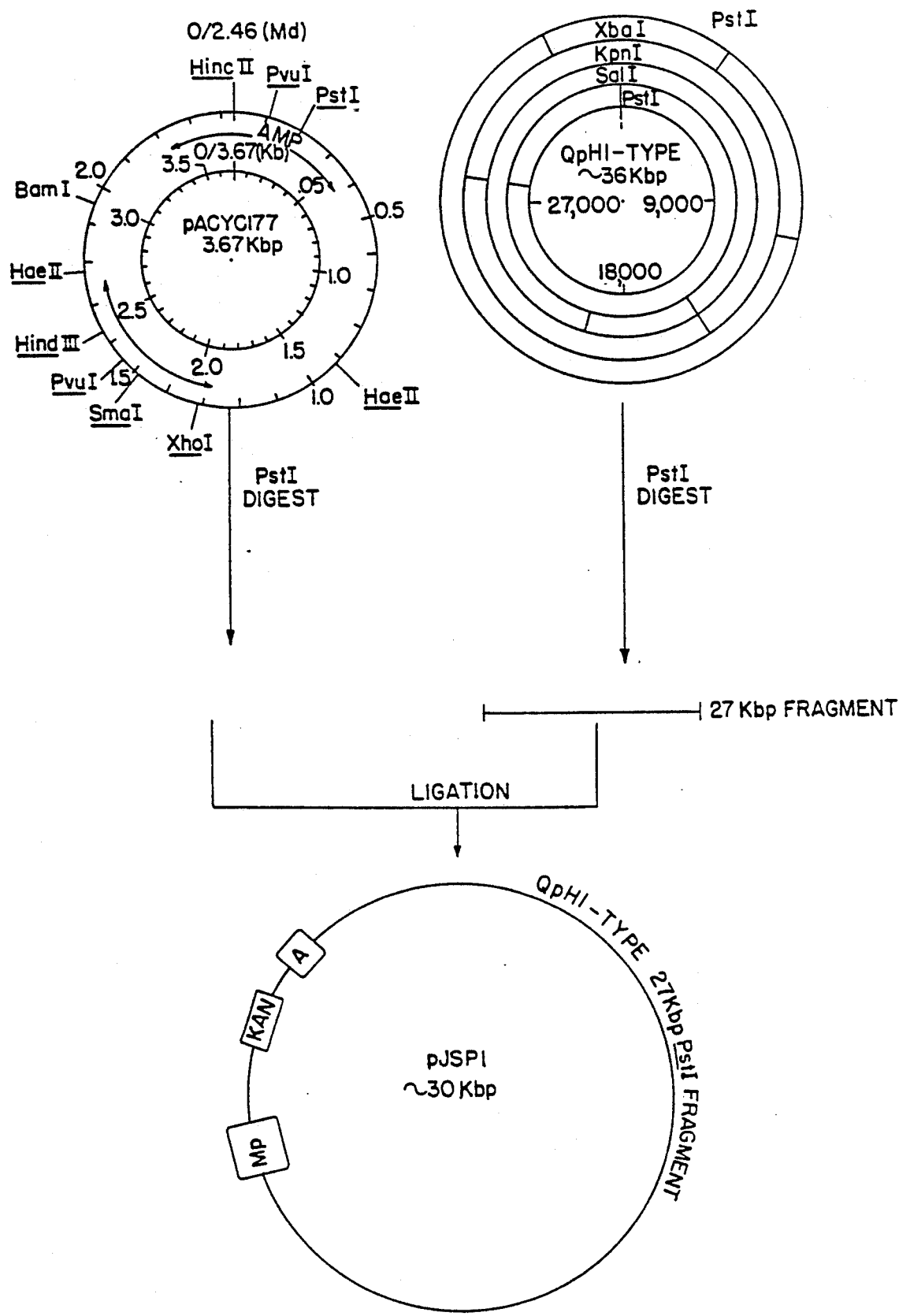
FIG. 7 illustrates the construction of recombinant plasmid pJSP1.

As noted above, current diagnosis of *Coxiella burnetii* infection is a complicated, time-consuming, and hazardous procedure. As a result this disease usually goes undiagnosed or misdiagnosed. Although physicians are required to report *C. burnetii* infections in 34 states, it is difficult to differentiate the acute disease symptoms of *C. burnetii* infection from influenza, primary atypical pneumonia, bacterial pneumonia, or a number of other pneumonia- or flu-like symptoms caused by a variety of etiological agents. Current procedures require isolation of *C. burnetii* from the patient or demonstration of a significant rise in specific antibody titer in successive serum samples. Isolation of *C. burnetii* requires specialized and expensive culture techniques, and should be performed in P-3 isolation facilities. While serologic detection is simpler and safer, confirmatory diagnosis of *C. burnetii* infection may take weeks. Currently, there is no way to predict from existing diagnostic tests, or from the initial symptoms, whether *C. burnetii* infection will result in chronic or acute disease.

Recently, examination of the virulence of a variety of *C. burnetii* strains resulted in the detection of a plasmid in the Nine Mile strain of *C. burnetii* (Samuel et. al., *Infect. & Immun.* 41:488–493, 1983; Mallavia et al., *Microbiology, Amer. Soc. for Microbiol.*, Wash., D. C., pp. 293–296, 1984). Prior studies of the role of plasmids in other organisms indicated that plasmids may encode virulence determinants. Efforts leading up to the present invention, for instance, have shown that the *C. burnetii* plasmid designated QpHl is rickettsia-specific, with a molecular mass of $2.4 \times 10^6$ daltons, and that it is present in low copy number. Plasmid DNA, which was present in both phase I and phase II variants, did not appear to be overtly involved in phase variation, however, and functions of the plasmid DNA remained cryptic (Samuel et al., *Infect. & Immun.* 49:775–779, 1985).

Representative of acute disease causing genomic groups of *C. burnetii* are the Nine Mile phase I isolates with respect to their lipopolysaccharides (LPS) and by having a representative cryptic plasmid of the QpHl-type. In contrast, isolates from chronic cases have LPS that are electrophoretically and antigenically distinct from those acute isolates.

Within the present invention, *C. burnetii* isolates were analyzed to determine how widely the QpHl-type plasmid sequences were distributed, and the extent to which they were conserved. Analyses of a large number (>40) of *C. burnetii* isolates demonstrated the stability of the QpHl-type plasmid sequences in isolates obtained from around the world over a 40-year time span. The large majority of the isolates (~30) analyzed contained a plasmid which appeared to be identical to the QpHl-type plasmid.

Chronic isolates lack the QpHl-type plasmid. However, isolates from three chronic endocarditis patients and two goat abortions shared a second representative plasmid type (designated QpRS) that was very similar to the QpHl-type plasmid, as measured by hybridization and restriction enzyme analysis. Comparative restriction enzyme digests and mapping studies indicated that the QpRS-type plasmid has unique regions, and is approximately 39 kilobase pairs (kbp) in length. Similarly, the QpHl-type plasmid is approximately 36 kb in size. Analysis by Southern blot indicated that QpHl-type plasmids and QpRS-type plasmids are approximately 80% homologous (FIG. 1). Analysis of four additional endocarditis isolates revealed that, although there was considerable homology of genomic DNA with QpRS-type and QpHl-type plasmids, the restriction endonuclease digestion patterns of these four isolates were considerably different from those of QpRS and QpHl plasmid types. An inability to isolate plasmids from this third group of *C. burnetii* suggested that plasmid sequences may have been integrated into the rickettsial chromosome.

A third representative plasmid type, termed QpDG, has recently been purified from *C. burnetii* isolates from feral rodents collected near Dugway, Utah.

The present invention, along with application Ser. No. 927,779 and application Ser. No. 795,207 which are incorporated herein by reference, provides the first clear evidence that differences exist between *C. burnetii* isolates which cause distinguishable diseases. In particular, the present invention provides superior methods for the rapid detection of *C. burnetii*, and additionally presents a method for predicting whether a particular *C. burnetii* infection will result in acute or chronic disease. The methods of the present invention do not require culture or serologic analysis of the biological sample, but rather utilize specific hybridization of a labeled DNA probe to DNA of cells obtained from a patient. If the patient's cells are infected with *C. burnetii*, the labeled DNA probe will hybridize to the rickettsial DNA, and may subsequently be detected. A second labeled DNA probe, which selectively hybridizes to C. burnetii strains associated with chronic disease, is used for hybridization to DNA of cells suspected of containing these *C. burnetii* strains. Utilization of this differentiation technique allows a clinician to identify patients which might require specialized treatment or attention.

The methods for detection and differentiation of *C. burnetii* isolates are also applicable to epidemiological studies of both human and animal populations. The simplification and decreased expense provided by the diagnostic assay for *C. burnetii* described herein is also useful in the veterinary setting through eradication of infected animals from domestic livestock herds. Such eradication is economically desirable to livestock owners, and would reduce or eliminate the animal reservoir responsible for human disease.

For many clinical specimens, detection of *C. burnetii* in biological samples may be optimized by concentration of the specimen. The concentrated specimen may then be immobilized onto a solid support to facilitate subsequent treatment, hybridization, and detection steps. Concentration, which may be accomplished by centrifugation, ensures that sufficient cellular material (containing the rickettsial DNA) is immobilized to permit detectable DNA-DNA hybridization. A preferred solid support for immobilization is a DNA-binding filter membrane. In addition, hydroxyapatite columns or other DNA-binding materials may be used. The DNA-binding filter membrane manufactured by NEN Research, Boston, Mass., is particularly preferred.

In a preferred embodiment, the cells are treated prior to hybridization, so as to expose the cellular DNA before performing the DNA-DNA hybridization step. The cellular DNA may be exposed by a variety of techniques, which include lysing the cells or rendering the cells permeable (Samuel et al., *Infect. Immunity* 49:775-79, 1983), or by the addition of 1.0 mg/ml proteinase K in TE buffer (10 mM Tris-HCl, 1 mM EDTA) at pH 7.5 and 1% sodium dodecyl sulfate (SDS) followed by incubation at 60° C. for 60 minutes. Subsequent treatment of the exposed cellular DNA, which generally includes immobilizing the DNA on a solid support, DNA denaturation, DNA neutralization, and heating under vacuum, is preferred. Prehybridization of the solid support after exposure of the cellular DNA and before DNA-DNA hybridization is also preferred (*Current Protocols in Molecular Biology*, Ausubel et al., ed., John Wiley and Sons, N. Y., Vol. 1, chap. 2, pp. 2.9.5-2.9.10, 1987).

As noted above, *C. burnetii*-specific DNA probes are labeled to facilitate detection of DNA-DNA hybridization. Preferred labels are radioisotopes and biotin. Radiolabels such as $^{32}P$, $^{3}H$, $^{35}S$ and $^{131}I$ are particularly preferred. Correspondingly, preferred hybridization detection systems are autoradiography and colorimetric assays, respectively.

In one embodiment of the present invention, a method for rapid detection of *C. burnetii* and a test for predicting whether a particular *C. burnetii* infection will result in acute or chronic disease has been developed. This method utilizes specific hybridization of a labeled DNA probe to DNA of cells obtained from a patient. The probes were developed using unique or shared plasmid sequences for detecting *C. burnetii*, and differentiating among organisms containing plasmid sequences associated with chronic disease from those harboring plasmid sequences associated with acute disease (FIG. 2). Within this embodiment, one aliquot of the sample is hybridized with a DNA probe that specifically hybridizes with *C. burnetii* DNA (this probe can be prepared from any of the shared DNA plasmid sequences as illustrated in FIG. 2), and another separate aliquot of the same sample is hybridized with a DNA probe containing DNA sequences that specifically hybridize with *C. burnetii* cellular DNA of strains associated with the capacity to cause chronic disease (such as the QpRS-type plasmid sequences as illustrated in FIG. 2, e.g., the internal Pst I fragment of the E fragment or an internal region of fragment A or portions thereof). If the first probe does not hybridize, *C. burnetii* is not present. If the first probe hybridizes, the second aliquot is used to determine whether a chronic strain of *C. burnetii* is present in the sample.

Another method for rapid detection of *C. burnetii* and differentiation between strains that cause chronic disease and those that cause acute disease is also based in part on the observation that the different strains contain different plasmid sequences. This method, which employs the polymerase chain reaction (PCR) (Saiki et al., *Science* 230:1350-54, 1985; Saiki et al., *Science* 239:487,91, 1988), requires knowledge of specific DNA sequences in the target region of DNA to be amplified. Based on this sequence information, two oligonucleotide primers are prepared: one complementary to the sequence on the (+) DNA strand, and the other to a downstream sequence on the (−) strand. Thus, the primers flank the region to be amplified, so that iterative cycles of Taq 1 DNA polymerase chain extension are used to generate multiple copies of the DNA that lies between the two primers, as described in U.S. Pat. No. 4,800,159 and incorporated herein by reference.

To utilize this technique for *C. burnetii* detection, a variety of primer sets may be chosen. For example, one set may be derived by sequencing the H' fragment from the QpH1 plasmid type, which is shared by all *C. burnetii* plasmids (homologous sequences are present in the plasmidless strains of *C. burnetii* as well). In one embodiment of the present invention, a subfragment (∼554 bp in length) of the H' fragment was utilized. Oligonucleotide primers were then prepared that flanked the ∼554 bp portion of this region, so that when these H' primers are used in a PCR-containing *C. burnetii*, a DNA fragment is produced. The PCR produces up to a $10^7$ amplification of the target sequences. For example, a sample containing $10^{-14}$ g *C. burnetii* DNA produced sufficient DNA (in a 20-µl reaction mix) to be easily observed by ethidium bromide staining of the agarose gels. Southern blotting or DNA sequencing can be used to confirm that the DNA generated is the same as in the target sequence. When Southern blotting is used in conjunction with PCR, the test is sensitive with as few as 1-2 *C. burnetii* cells. The advantages of such assay systems are evident in studying the efficiency of antibiotic therapy, mechanisms of pathogenesis, and/or mechanisms of persistence.

In order to differentiate between the different *C. burnetii* strains, a second PCR reaction may be conducted using primers specific for DNA sequences that are shared by QpRS-type plasmids and the plasmidless strains of *C. burnetii*. These primers copy unique regions of the plasmid type QpRS, such as the A or E region (FIG. 2). As in the first detection method, the first reaction detects the presence of *C. burnetii*. If the ∼554-bp fragment is produced, the sample contains *C. burnetii*. If the first PCR sample generates the ∼554-bp fragment, a second PCR is necessary to determine whether the strain detected contains DNA sequences associated with the acute or chronic disease. The presence of specific fragments (for example, target from A or E sequence) in the second PCR indicates that the sample contains one of the chronic-disease-causing strains; if not, it contains a strain that causes only acute disease.

It is evident to those skilled in the art that once the DNA sequence of the target region to be amplified is known, any number of primers may be employed in the detection or differentiation between strains of *C. burnetii* capable of causing chronic or acute disease. For example, partial DNA sequences for the H' and G' regions of a QpH1 plasmid type, as well as for the A and E regions of a QpRS plasmid type are disclosed in FIGS. 3 through 6, respectively. Restriction sites are shown in bold type, and primer regions are indicated by bold, underlined type (underlined region in FIG. 6 indicates a protein coding region).

Based upon these known sequences, exemplary primers for each region which have been utilized in the present invention are given below.

1) H' fragment primers (yielding a ∼554-bp fragment):
   5'TGAGGTTCTTTGAATAAGCCAAATGAT3', and
   5'AATTGCTATCACTGAGGGTGACGGCAC3'.
2) G' fragment primers (yielding a ∼1258-bp fragment):
   5'TGACAAATAGAATTTCTTCATTTTGATG 3', and
   5'CGCTTATTTTCTTCCTCGAATCTATGAAT 3'.
3) A fragment primers (yielding a ∼378-bp fragment):
   5'TAACCCTTATGCGTATTGCGACGGCGAT 3', and
   5'CTTGGCTAGCCCGGAGATTAATTTTTTG 3'.
4) E fragment primers (yielding a ∼1052-bp fragment):
   5'CTCGTACCCAAAGACTATGAATATATCC 3', and
   5'CTGTTAATTCACTAATCGATTCCATTGAT 3'.

Utilizing the above embodiments of the present invention, a variety of tests may be employed to detect and/or differentiate C. burnetii strains capable of causing acute or chronic disease. For example, by utilizing probes as primers derived from (1) unique regions of QpRS-type plasmids (e.g., fragment E), (2) unique sequences of QpH1-type plasmids (e.g., fragment G'), and (3) shared sequences between both types of plasmids (e.g., fragment H'), a large number of tests would be evident to those skilled in the art, including the following:

H' positive and E negative→acute strain
H' positive and E positive→chronic strain
H' negative and E negative→no C. burnetii in sample
H' positive and G' negative→chronic strain
H' positive and G' positive→acute strain
H' positive and G' negative→no C. burnetii in sample In still another embodiment of the present invention, a method is disclosed for identifying the genomic grouping of C. burnetii isolates and determine the pathogenicity of such isolates. This method permits the classification of any future related isolates and the subsequent use of such isolates in the detection and/or differentiation of C. burnetii strains capable of causing acute or chronic disease.

To summarize the examples which follow, Example I describes methods for the rapid detection of C. burnetii DNA in a biological sample. Example II describes a method for differentiating C. burnetii strains that are capable of causing chronic disease from those that are capable of causing acute disease. Example III describes the expression and sequencing of genes cloned from QpH1-type and QpRS-type plasmids harbored by acute and chronic strains of C. burnetii, respectively. Example IV describes the genomic groupings of C. burnetii stains and the use of specific cellular DNA regions of those strains to detect and/or differentiate C. burnetii strains capable of causing acute or chronic disease.

The following examples are offered by way of illustration and not by way of limitation.

EXAMPLE I

Detection of C. burnetii Growth and Purification

Rickettsia were propagated in the yolk sacs of embryonated White Leghorn eggs obtained from flocks fed an antibiotic-free diet. The embryonated eggs were inoculated at day 6 with appropriate stocks of C. burnetii diluted in 0.1% skim milk, incubated at 37° C., and candled daily. Eggs with dead embryos were discarded. The infected yolk sacs of viable embryos were harvested 8 days after inoculation with the agent, and the rickettsial organisms were partially purified as described by Hendricks and Mallavia (J. General Microbiol. 130:2857–2863, 1984). Thirty to sixty grams of yolk sacs was added to 100 ml of cold SP buffer (0.25M sucrose, 140 mM potassium chloride, 10 mM potassium phosphate, pH 7.2). The mixture was blended three times (30 seconds each) in a Sorvall (Dupont-Sorvall, Wilmington, Del.) homogenizer. The resultant homogenate was then centrifuged at 16,000×g for 45 minutes in a refrigerated centrifuge. The supernatant and lipid layers were discarded, and the rickettsia-containing pellet was carefully resuspended in 100 ml cold SP buffer, using a 12-gauge cannula and syringe.

The mixture was centrifuged at 200×g for 10 minutes, and the rickettsia-containing supernatant was centrifuged again at 21,000×g for 45 minutes. The pellet was resuspended in 9 volumes of SP buffer and recentrifuged. The pellet was again resuspended in SP buffer and passed through an AP-20 filter to remove residual Celite and mitochondria. The filtrate was then centrifuged through a 30% sucrose-SP buffer clearing gradient; the pellet was resuspended and banded by isopyknic centrifugation in 30% to 60% linear sucrose gradients (Thompson et al., Biochem. J. 125:365–366, 1971). The gradients were centrifuged at 100,000×g for 120 minutes at 4° C. The rickettsial bands were harvested, diluted in SP buffer, and the dry weight of the organisms was determined spectrophotometrically (Burton et al., J. Bacteriol. 122:316–324, 1975). This was done by determining the Klett reading of organisms in solution and converting it to cell number, using a standard curve (Hackstadt & Williams, J. Bacteriol. 148:419–425, 1981).

Preparation of DNA from Harvested Rickettsiae

Rickettsiae harvested from yolk sacs as described above were lysed by the addition of 100 µg/ml thermolysin and incubated for 60 minutes at room temperature; sodium dodecyl sulfate (SDS) was added to a final concentration of 1% (w/v). Thermolysin was used because of its broad proteolytic activity and absence of nuclease activity. Gentle but thorough mixing at room temperature for 10 to 20 additional minutes was required to effect complete lysis (Samuel et al., Infect. Immun. 41:488–493, 1983). The crude DNA lysate can be used for plasmid isolation, or can be further purified by extraction with phenol/chloroform. The purified DNA is in the aqueous phase following phenol/chloroform extraction.

Isolation of Plasmid DNA

For plasmid isolation, the crude DNA lysate was mixed with CsCl (to a 4.5M final concentration) and ethidium bromide (~600 µg/ml). The resultant mixture was centrifuged to equilibrium (48 hours at 45,000 rpm in a Ti 60 [Beckman Instruments, Inc., Palo Alto, Calif.] rotor). The plasmid DNA/ethidium bromide complex, which bands at a density greater than that of chromosomal DNA, was visualized by fluorescence. The fluorescent DNA bands were located using long-wave ultraviolet light, and the individual bands were collected from the top, using a 12-gauge cannula and syringe. Standard extraction with chloroform, isoamyl alcohol, and ether was used to remove the ethidium bromide from each preparation (Maniatis et al., Molecular Cloning: A Laboratory Manual, Cold Spring Harbor Laboratory, Cold Spring Harbor, N.Y., 1982). The DNA samples were then extensively dialyzed against TE (10 mM Tris (pH 7.4), 1 mM EDTA) at 4° C. The resultant solution was adjusted to contain 250 mM sodium acetate, then precipitated overnight with 2 vol of 100% ethanol at −20° C. for 45 minutes at 15,000 rpm in an SS34 rotor (Dupont-Sorvall). The DNA was washed within 70% ethanol, repelleted, and resuspended in TE (Currier & Nester, Anal. Biochem. 76:431–441, 1976).

Generation of Recombinant Plasmid pJSP1

A QpH1-type plasmid was obtained from the Nine Mile strain of C. burnetii (ATCC No. ATCVR-625), and purified using the procedure described above (Samuel et al., Infect. Immun. 41:488–493, 1983). Purified QpH1 plasmid type DNA was digested with restriction endonuclease Pst I and electrophoresed in a preparative Tris-acetate-agarose gel (1.0%; Maniatis et al., Molecular Cloning: A Laboratory Manual, Cold Spring Harbor Laboratory, Cold Spring Harbor, N.Y., 1982).

To separate the various restriction fragments, electrophoresis was continued until the approximately 27 kbp piece was well separated from the 8.5-kbp fragment of the QpH1-type plasmid (FIG. 7). A well was cut in front of the 27 kbp plasmid, and a piece of dialysis tubing was placed in the well in a manner which blocked the entry of the DNA into the gel. The approximately 27 kbp DNA was then collected by electro-elution into the well against the dialysis tubing, and the DNA was removed. The fragment from the QpH1-type plasmid was electrophoresed and extracted two times with phenol/chloroform. The resultant material was then ethanol precipitated. The pellet was resuspended in 200 μl $H_2O$ and 25 μl of 3M sodium acetate, pH 5.2. The resultant solution was ethanol-precipitated, and the pellet rinsed in 10% ethanol and resuspended in TE. The 27-kbp fragment of QpH1-type plasmid was ligated with pACYC 177 (Chang & Cohen, J. Bacteriol. 134:1141–1156, 1978), which had been digested to completion with Pst I. Several vector-insert ratios were prepared, and a mixture of the best ligations, as determined by gel analysis, were used to transform E. coli RR1.

A number of different vectors could be used in this step. The inventors selected pACYC 177 because it was a nontransmissible derivative of p15A and transfers poorly, even in the presence of an F plasmid. The pACYC 177 plasmid vector is 3.7 kbp in size and contains both ampicillin and kanamycin resistance markers. This vector has a single Pst I cleavage site in the ampicillin resistance region, which allows the use of insertional inactivation as a method of detecting successful recombinant fragments. It should be noted that vectors containing a tetracycline resistance marker should not be used, since tetracyclines are the drugs of choice in the treatment of acute C. burnetii disease.

Following enzyme inactivation, the DNA was dephosphorylated with calf intestinal alkaline phosphatase (repurified; Sigma, St. Louis, Mo.). The pACYC 177 was combined with a 3M excess of the 27 kbp Pst I fragment of the QpH1-type plasmid, and the mixture was ligated with $T_4$ DNA ligase (Maniatis et al., Molecular Cloning: A Laboratory Manual; Cold Spring Harbor Laboratory, Cold Spring Harbor, N.Y., 1982). This ligation mixture was transformed in E. coli RR1 using the standard calcium chloride transformation technique (Clewell, J. Bacteriol. 110:667–676, 1972). Single-colony isolates were selected and tested for the presence of QpH1-type plasmid sequence using the method of Birnhoim and Doly (Nucl. Acid Res. 7:1513–1523, 1979). The isolates obtained contained the sequences in either a 5'→3' orientation. Either one will work as a probe. pJSP1 consists of the 5'→3' orientation (Mallavia et al., Microbiology, Amer. Soc. for Microbiol., Washington, D.C., pp. 293–296, 1984). The transformed bacteria were propagated, and single-colony isolates containing cloned QpH1-type plasmid DNA were selected by insertional inactivation of antibiotic resistance ($Kan^r$ and $Amp^s$).

Following amplification in E. col RR1, the structure of the plasmid was verified by restriction mapping and Southern techniques (Southern, Molec. Biol. 98:503–517, 1975). The structure of the resultant recombinant plasmid, pJSP1, is shown in FIG. 3. This construct was used to produce a labeled DNA probe for detecting the presence of C. burnetii in biological samples.

Purified pJSP1 DNA was digested to completion with Pst I and electrophoresed in a preparative Tris-acetate-agarose gel. The 27 kbp restriction fragment was separated from the ~3.7 kbp of pACYC 177 and the 27 kbp fragment was collected using the same method described earlier in this section. The plasmid type QpH1-derived 27 kbp probe was nick-translated using either $^{32}P$- (Maniatis & Klein, Proc. Natl. Acad. Sci. 72:1184–1188, 1975) or biotin-labeled (Leary et al., Proc. Natl. Acad. Sci. 80:4045–4049, 1983) nucleotides. The labeled DNA probe was hybridized to cellular DNA, which had been immobilized on a DNA-binding filter membrane (NEN Research, Boston, MA), using either Southern (Southern, Molec. Biol. 98:503–517, 1975) or dot blot hybridization protocols.

Assay for Detection of C. burnetii

Ten to twenty ml of whole blood was centrifuged to concentrate the white blood cells, which was used as a "buffy coat." The buffy coat was placed on a two-step gradient of 5 ml of 40% Ficoll-Hypaque (Winthrop Laboratories, Sterling Drug, Inc., New York, N.Y.) on top of 5 ml of 60% Ficoll-Hypaque, both diluted in phosphate-buffered saline (PBS). White cells were isolated from the 40%–60% interface, washed in PBS, and resuspended in a small volume (~20 μl) of PBS. The purified white blood cells, and the rickettsial cells contained within them, were absorbed on a DNA-binding filter membrane (NEN Research). These membranes were then treated by being placed sequentially on 3MM Whatman paper soaked with an appropriate solution. Cells were first lysed with a solution of 0.2% (w/v) SDS/0.5M NaOH/1.5M NaCl. The rickettsial DNA was then denatured with 0.5M NaOH/1.5M NaCl, and neutralized with a solution of 0.5M Tris-HCl (pH 7.5)/1.5M NaCl. Each treatment was carried out for 15 minutes. The membrane was heat-treated under vacuum at 80° C. for 2 hours, then prepared for hybridization.

Prior to hybridization, the membrane was pre-hybridized with a solution of 50% (v/v) deionized formamide, 0.75M NaCl, 0.075M sodium citrate, 20 mM Tris-HCl (pH 8.0), 1 mM EDTA, and 20 μg/ml denatured salmon sperm DNA. Hybridization was then carried out by the addition of >5 ng/ml of a heat-denatured, high specificity activity, nick-translated C. burnetii-specific DNA probe (pJSP1), which was previously described. Hybridization was performed at 42° C. for 20 to 24 hours. Non-hybridized, labeled DNA probe was then removed by washing the filter in 0.1X SSC (20X SSC consists of 175.3 g NaCl and 88.2 g of sodium citrate/liter, pH 7.0), 0.1% (w/v) SDS, and 5 mM EDTA.

Hybridized, radiolabeled, C. burnetii-specific DNA probe was detected by autoradiography. Hybridized, biotinylated C. burnetii-specific DNA probe was detected by an avidin-biotin enzyme-activated (alkaline phosphatase or horseradish peroxidase) colorimetric detection system.

As a simplified alternative to the assay for detecting C. burnetii set forth above, whole blood was diluted with an equal volume of physiological saline. The blood (up to 8 ml), was then layered onto 3 ml of Ficoll-Paque (Pharmacia, Piscataway, N.J.) and centrifuged for 10 minutes at 2300 rpm in a Beckman TJ6 centrifuge at room temperature. The white cell layer was removed, and washed by centrifugation for 15 minutes at 2300 rpm at 4° C. in physiological saline. The resultant cell pellet was resuspended in saline G and deposited onto BA85 nitrocellulose filters (Millipore Corporation, Bedford, Mass.) using a dot blot, slot blot, or other filtration apparatus. To these cells, 5 ml of lysing solution (1% SDS, 10 mM EDTA, 10 mM Tris, pH 7.5, 150 mM NaCl, and 50 ug/ml proteinase K preheated to 60° C.) was added. The cells were allowed to sit in this solution for 15 minutes. After lysis, the cells were rinsed twice (5 ml each) with saline. DNA was treated with 5 ml denaturing solution (1.5M NaCl and 0.5 m NaOH); after 15 minutes, this solution was removed by filtration and 5 ml of neutralizing solution (1M Tris HCl, pH 7.0, 1M NaCl) was added and allowed to set for 5 minutes at room temperature. Following filtration of neutralizing solution, the filter-bound DNA was washed twice with 2X SSC. The filters were then dried under vacuum at 80° C. for 2 hours and prepared for hybridization. Hybridizations were carried out as previously described, with the exception that the final wash used 1X SSC. The higher stringency or homology provided by these conditions decreased any likelihood of false positives in either the detection of C. burnetii or in the differentiation between chronic and acute strains.

Detection of C. burnetii Using Blood Samples

Figure 8A:
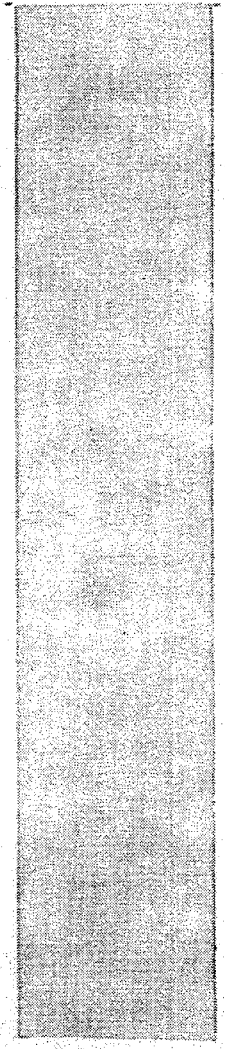
Figure 8B:
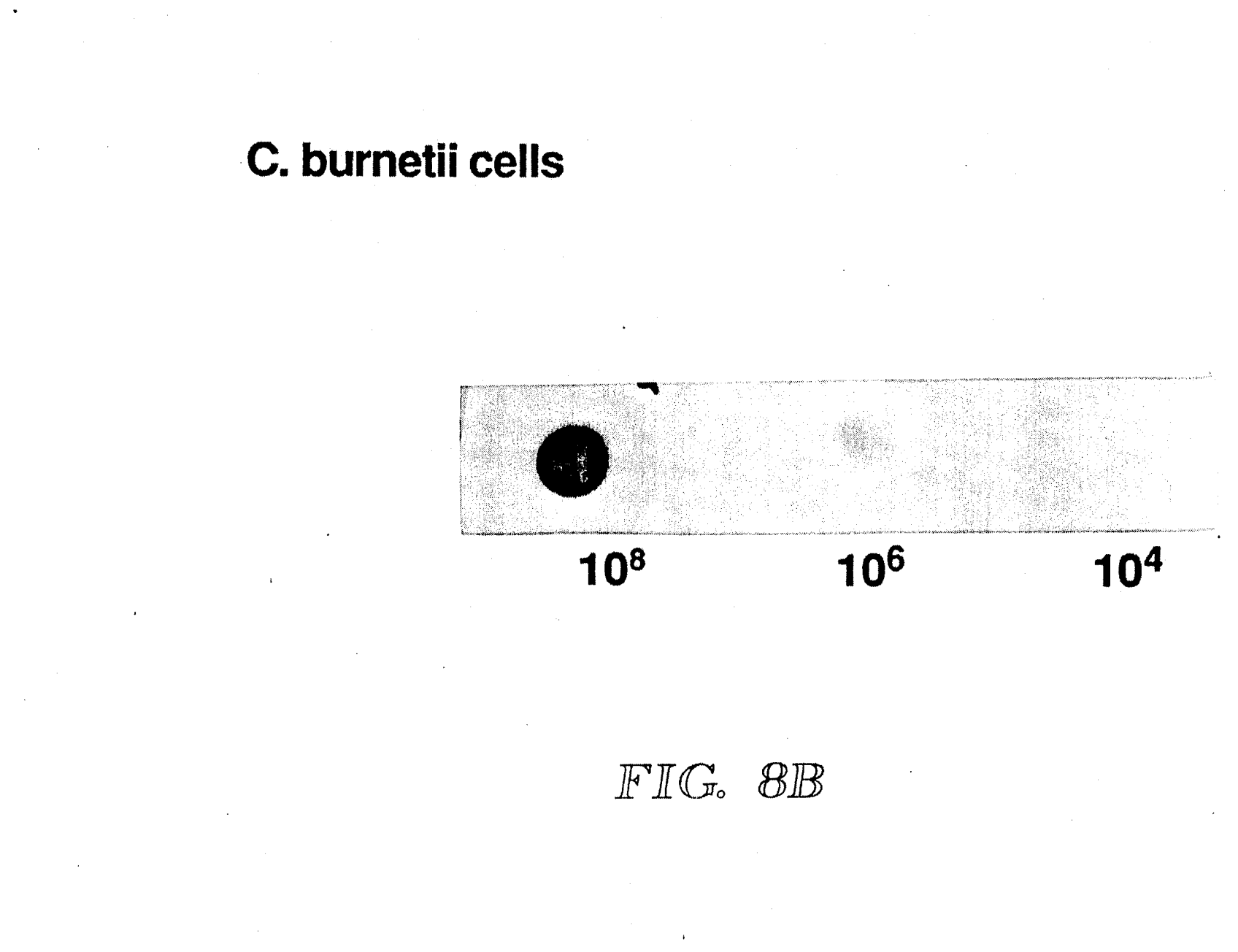
Figure 8C:
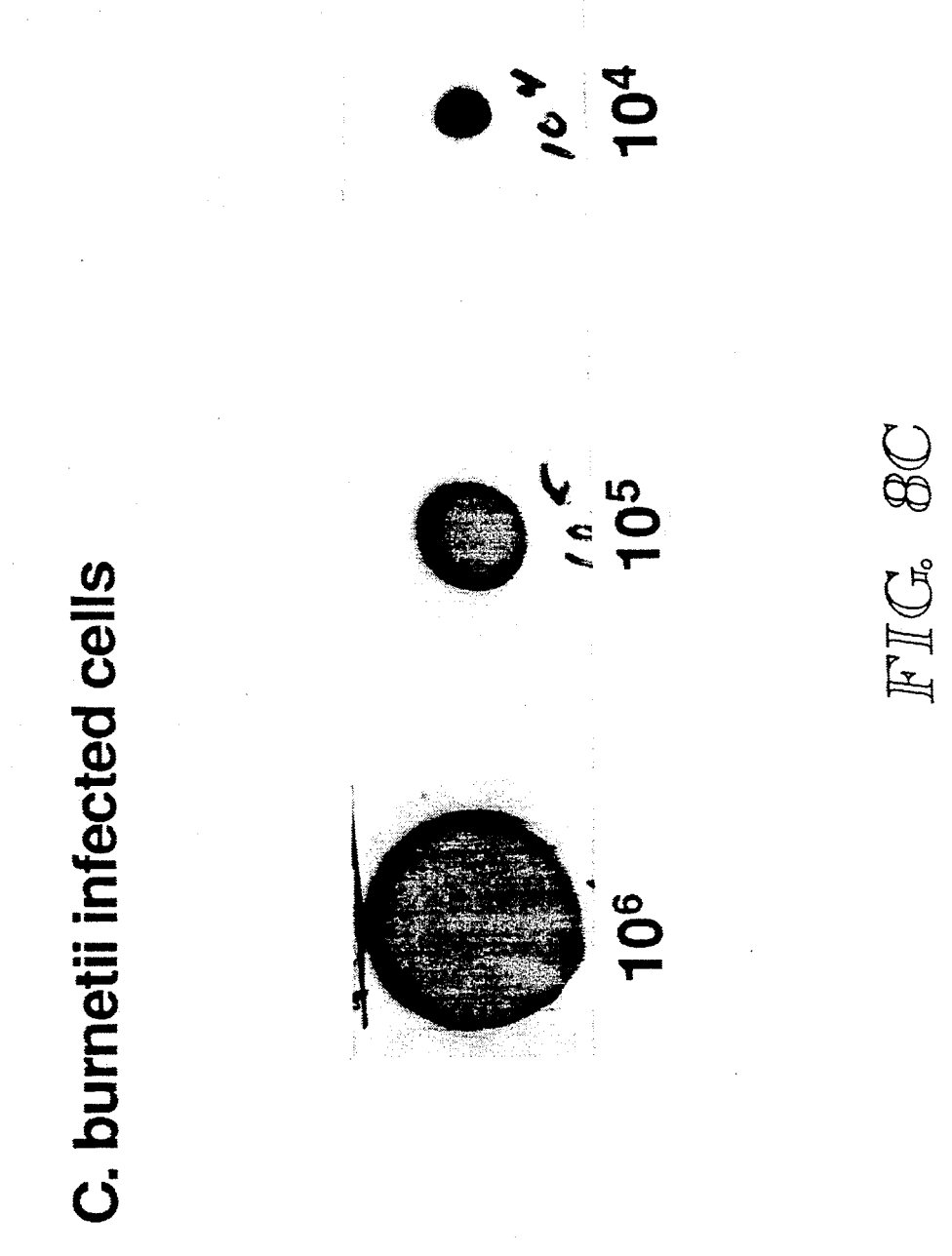

Referring to FIG. 8, using the simplified assay system set forth above, C. burnetii has been detected in the white blood cells isolated from 1 ml of peripheral guinea pig blood infected 4 to 5 days earlier (FIG. 8A). Using $^{32}$P-labeled probe (specific activity $5 \times 10^5$ cpm/ml) in controlled experiments, one can detect $10^4$ C. burnetii cells, as shown in FIGS. 8B and 8C. DNA from a million WBC had no effect on the hybridization signal from rickettsial DNA. Differential diagnosis between rickettsial strains required $10^5$ organisms under these conditions because of the smaller probe size. However, it will be evident to those skilled in the art that probes of higher specific activity as well as signal-intensifying techniques may be utilized in order to increase sensitivity (and, therefore, decrease the numbers of rickettsia required).

Detection of C. burnetii Using Urine Samples

It is also possible to detect the presence of C. burnetii in urine. It is important to note that the concentrations of rickettsia in urine [$10^2$–$10^3$ guinea pig infectious doses/ml (GPID)] are much lower than are observed in blood ($10^4$–$10^6$ GPID/ml). In this assay, the urine can be either centrifuged to pellet the organisms or filtered directly through the nitrocellulose filter. Subsequently the cells are treated with lysing solution, rinsed, and the DNA treated as set forth above in the simplified assay procedure.

EXAMPLE II

Differentiation of C. burnetii Strains

A QpRS-type plasmid was obtained from the Priscilla Q177 strain of C. burnetii, which is available from either Rocky Mountain Laboratories, National Institute of Allergy and Infectious Disease, Hamilton, Mont., or from Dr. L. P. Mallavia, Dept. of Microbiology, Washington State University, Pullman, Wash., who has the same on deposit in his laboratory. The Priscilla Q177 strain of C. burnetii was grown and purified in the same manner described in Example I, and QpRS-type plasmid DNA was obtained by using the purification scheme outlined for the QpH1 plasmid type.

C. burnetii plasmid of the QpRS-type contains unique DNA sequences which are not present in QpH1 plasmid types (see FIG. 2), and these unique sequences have been associated with C. burnetii strains that have the capacity to cause chronic disease. These unique QpRS-type plasmid sequences have been utilized in a second radiolabeled DNA probe, which can be used to differentiate C. burnetii isolates which cause chronic disease from those which cause acute disease.

Generation of Recombinant Plasmid pOB1

Figure 9:
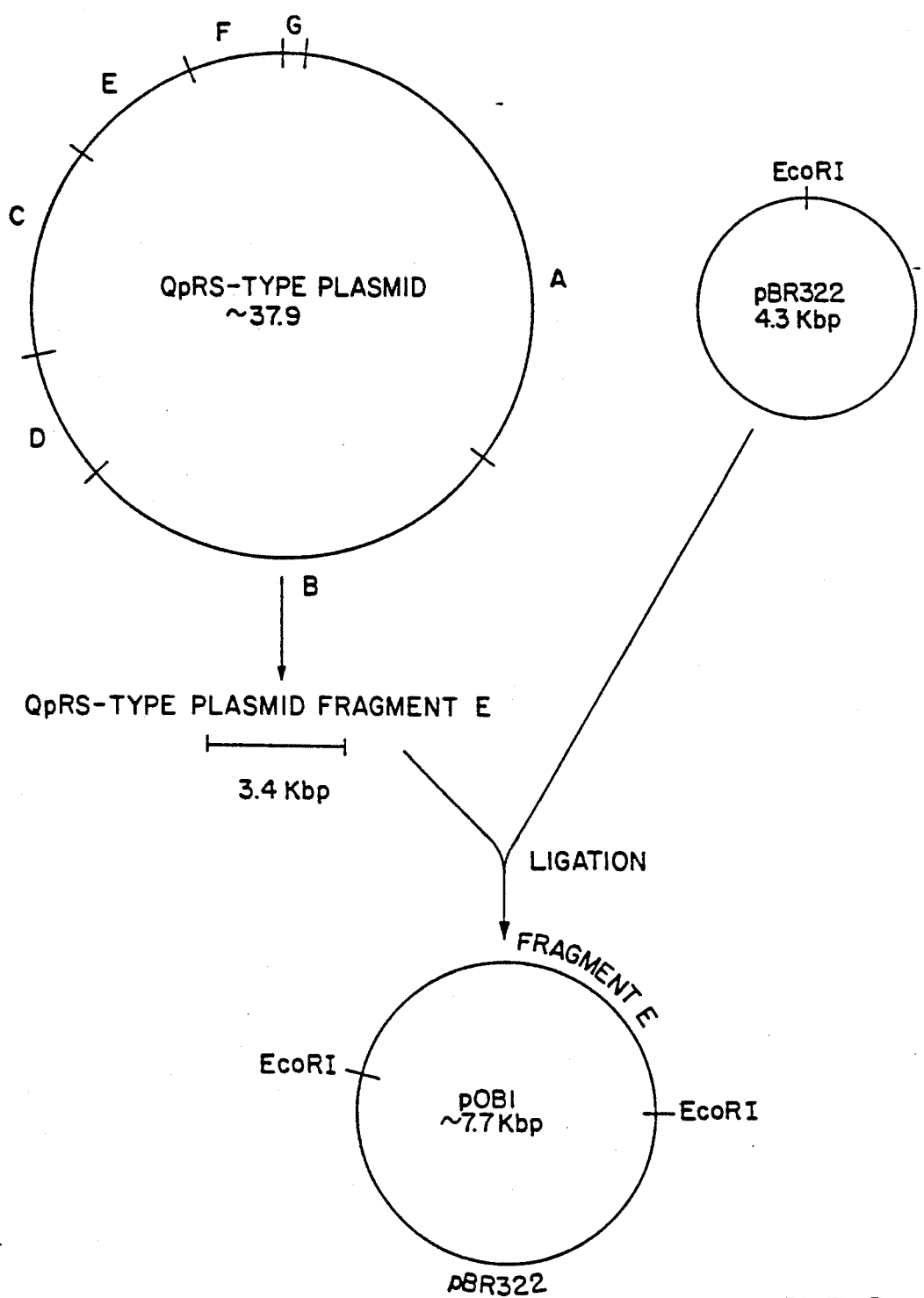
FIG. 9 illustrates the construction of recombinant plasmid pOB1.

The ~3.6 kbp Eco RI fragment of plasmid type QpRS, designated fragment E, was cloned into the Eco RI site of plasmid pBR322 to produce the recombinant plasmid pOB1 (FIG. 9). Plasmid pBR322 was fully cleaved with Eco RI; and following enzyme inactivation, the DNA was dephosphorylated with calf intestine alkaline phosphatase (repurified; Sigma, St. Louis, Mo.). The pBR322 DNA was combined with a 3M excess of the ~3.6 kbp QpRS-type plasmid fragment E, and the mixture was ligated with T$_4$ DNA ligase (Maniatis et al., *Molecular Cloning: A Laboratory Manual*, Cold Spring Harbor Laboratory, Cold Spring Harbor, N.Y., 1982). This ligation mixture was transformed into *E. coli* HB101, using the standard calcium chloride transformation technique (Clewell, *J. Bacteriol.* 110:667–676, 1972). Single-colony isolates were selected and tested for the presence of plasmid type QpRS-specific sequences, using the method of Birnboim and Doly (*Nucl. Acid Res.* 7:1513–1523, 1979).

The pOB1 recombinant plasmid was amplified and used to produce a labeled DNA probe that can differentiate C. burnetii strains capable of causing hepatitis, chronic endocarditis and other chronic infections from those capable of causing acute disease.

Assay for Differentiation

Figure 10:
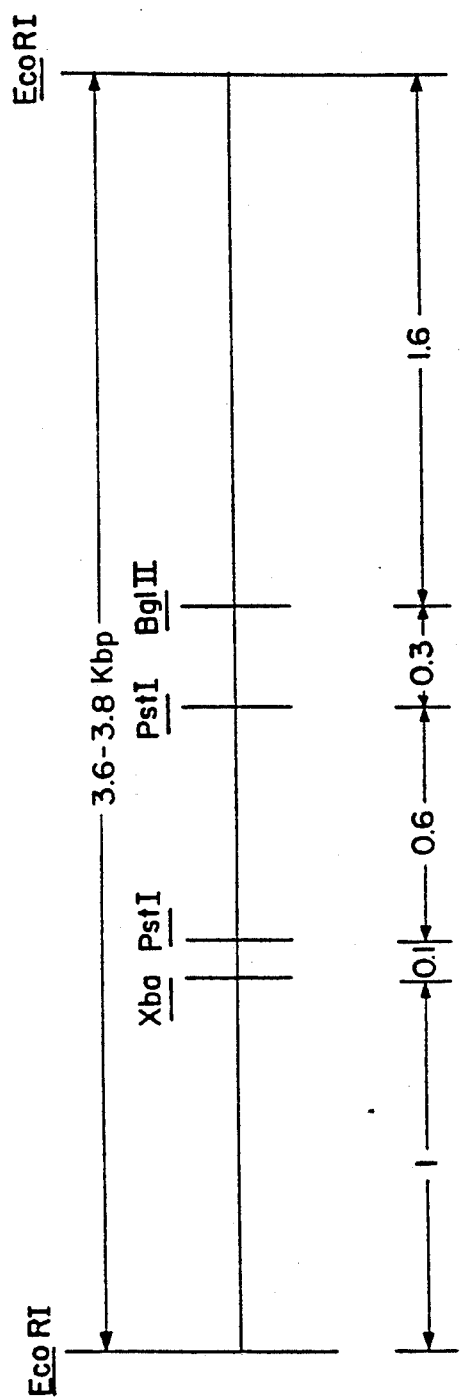
FIG. 10 illustrates a restriction endonuclease map of the E fragment of plasmid type QpRS.

The plasmid type QpRS-derived probe, which recognizes C. burnetii DNA that is associated with chronic disease, was prepared by isolating and purifying pOB1. The plasmid DNA was digested to completion with Eco RI and electrophoresed to separate pBR322 sequence from the ~3.6 kbp QpRS-type plasmid fragment E. The ~3.6 kbp fragment was collected using the procedure outlined for QpH1-type plasmids and nick-translated with $^{32}$P- or biotin-labeled nucleotides, as described above. While the whole ~3.6 kbp fragment of plasmid type QpRS can be used for differential diagnosis, a small portion of this fragment (~100 bp) has sequence homology to the QpH1-type plasmid and will therefore cross react at low stringencies. In order to eliminate any chance of cross reactivity, the large Xba fragment (~2.6 kbp), or the internal ~695 bp Pst I, or the fragment coding for the cbE gene can be used as probes (see FIG. 10). Cells suspected of containing C. burnetii were concentrated from biological samples and immobilized on a DNA-binding filter membrane (NEN Research). The cellular DNA was treated and prehybridized, as previously described. The cellular DNA was then hybridized with a labeled, plasmid type QpRS-derived DNA probe. Hybridization and detection of the labeled DNA probe was performed as described above, thereby allowing the detection of strains of C. burnetii associated with chronic disease.

The assay described above may be utilized in conjunction with the detection assays previously described, in order to differentiate strains of *C. burnetii* that are capable of causing acute disease from those strains capable of causing chronic disease. Samples that hybridize with sequences unique to the plasmid type QpHl-derived probe, but not with sequences unique to the QpRS-derived probe, indicate *C. burnetii* infection associated with acute disease. Samples that hybridize with unique sequences from both the QpHl and the plasmid type QpRS-derived probes indicate *C. burnetii* infection capable of causing chronic disease.

EXAMPLE III

Expression and Sequencing of Genes Cloned from Plasmids Harbored by Acute and Chronic Strains of *C. burnetii*

*C. burnetii* plasmids and/or chromosomal DNA were isolated as previously reported (Samuel et al., *Infect. Immun.* 41:448–493, 1983) from acute and chronic isolates of each disease-grouping of *C. burnetii*, including phase I Nine Mile RSA-493 (QpH1-type plasmid), Priscilla Q177 (QpRS-type plasmid), Dugway 7E9-12 (QpDG type plasmid), and the plasmidless-chronic isolates Ko Q229, S Q217, G Q212, and L Q216. Propagation and harvesting of *C. burnetii* was accomplished as previously described (Samuel et al., *Infect. Immun.* 41:448–493, 1983). *E. coli* strain DH5α or DH5αF⁻ (Bethesda Research Laboratory, Gaithersburg, Md.) was used as a recipient for all recombinant DNA. Transformants were grown at 37° C. in Luria-Bertain (LB) medium under appropriate antibiotic selection, with ampicillin (100 $\mu g/ml^{-1}$) for the pUC vectors (Viera et al., *Gene* 19:259-268, 1983) and kanamycin (25 $\mu g/ml^{-1}$) for the cosmid vector pHK17 (Klee et al., *J. Bacteriol.* 150:327-331, 1983). *E. coli* strain SG932 (lon100) was used for in vivo expression, and was grown at 30° C. in LB with ampicillin (100 $\mu g/ml^{-1}$).

Antibody Preparation Against *C. burnetii* Outer Membrane (OM)

An adult male New Zealand white rabbit was used to generate polyclonal antiserum against isolated OM of the Priscilla strain of *C. burnetii*. OM was purified by modification of a sodium dodecyl sulfate (SDS) extraction procedure (Hurlbert et al., *J. Gen. Microbiol.* 129:2241-2250, 1983). Briefly, ∼30 mg (dry weight) of freshly isolated cells were rinsed in 20 volumes of 10 mM HEPES buffer with 10% sucrose (w/v) (pH 7.5 at 4° C.), then pelleted by centrifugation at 12,100×g for 45 minutes at 4° C. The pellet was resuspended in 2 ml of HEPES and extracted in 0.4% SDS (w/v) as previously described (Hurlbert et al., *J. Gen. Microbiol.* 129:2241-2250, 1983). To liberate OM, four sonications on ice for 1 minute at constant cycle with a 1 minute cooling interval were used in place of a French pressure cell. Cell debris was removed from the suspended membranes by centrifugation at 12,100×g, as described above. The supernatant was then ultracentrifuged for 1 hour at 4° C., at 260,000×g, in a Beckman 60Ti rotor. The insoluble transparent pellet was resuspended and washed twice in the HEPES buffer, with ultracentrifugation between washes, as described above. The final pellet was resuspended in physiological saline (0.15N). Approximately 200 μg of OM protein in saline, as determined by the method of Lowry et al. (Lowry et al., *J. Biol. Chem.* 193:265-275, 1951), was emulsified in an equal volume of incomplete Freund's adjuvant and delivered as three subcutaneous 1-ml injections above the shoulders of the rabbit. Two subsequent booster injections of the same concentration and volume were administered in the same manner at 2-week intervals. Antiserum was collected 2 weeks after the second booster.

Construction of Recombinant DNA

QpRS-type plasmid DNA was purified from the *C. burnetii* Priscilla isolate by a previously described procedure (Samuel et al., *Infect. Immun.* 41:448-493, 1983). Purified QpRS-type plasmid was digested to completion with Eco RI and the resulting fragments were separated by electrophoresis through a 0.9% agarose gel prepared by standard methods (Maniatis et al., *Molecular Cloning: A Laboratory Manual*, Cold Spring Harbor Laboratory, Cold Spring, N.Y., 1982). The ∼3.6-kb-3.5-kb Eco RI fragment E of plasmid type QpRS did not hybridize when probed with end-labeled [$^{32}$P]-QpHl-type plasmid in Southern blot analysis.

Figure 11:
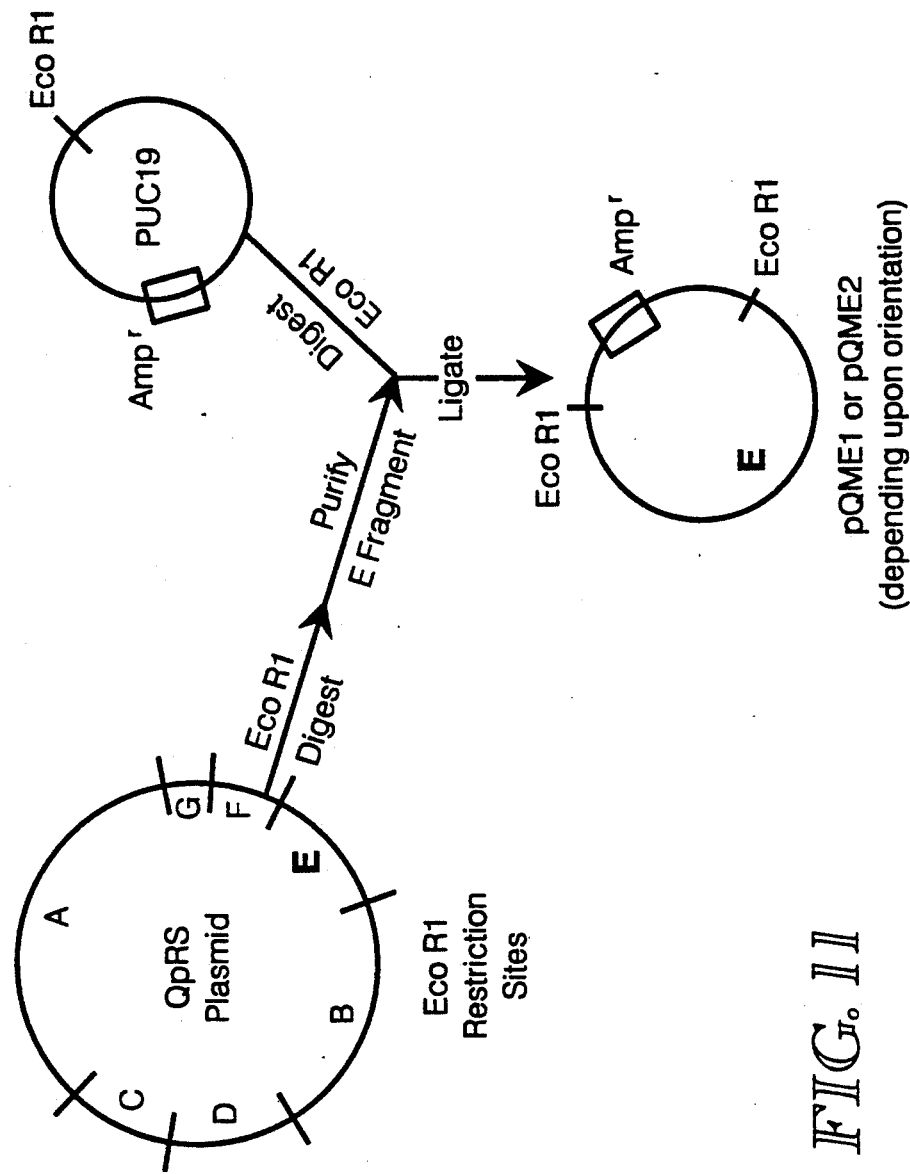
FIG. 11 illustrates the construction of plasmids pQME1 and pQME2.
Figure 12:
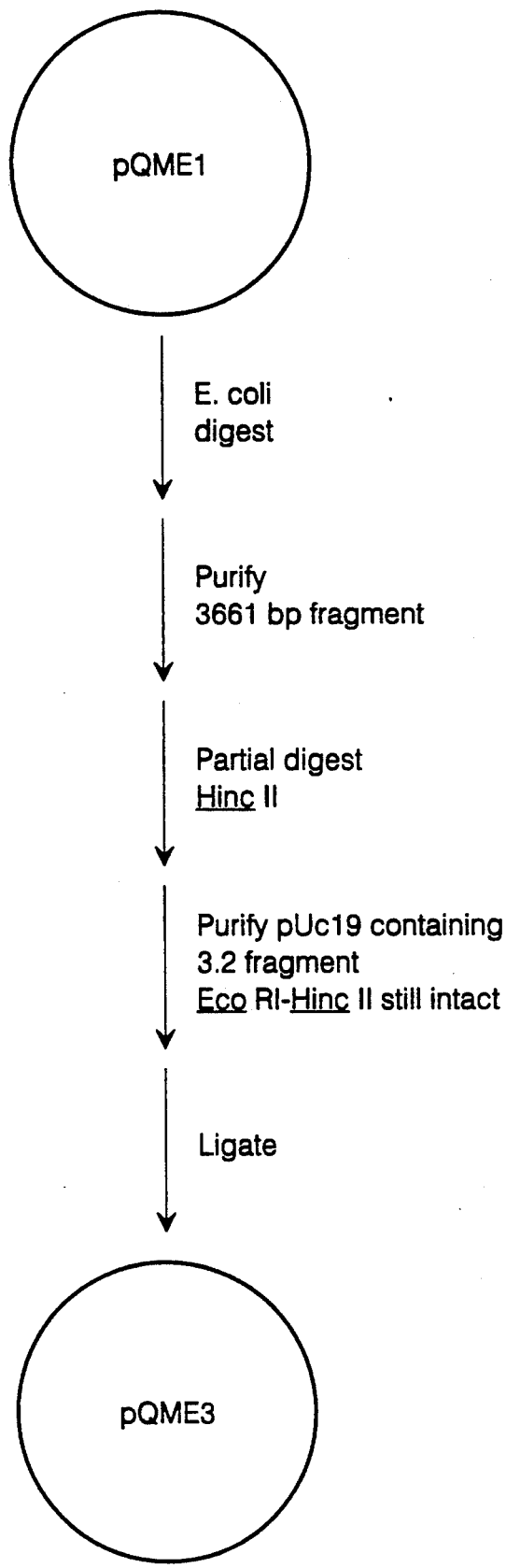
FIG. 12 illustrates the construction of plasmid pQME3.

Because of its uniqueness with respect to QpHl-type plasmid DNA, the QpRS-type plasmid E fragment was further subcloned and characterized. Briefly, the E fragment was excised from agarose gels and freed of agarose by Gene Clean (Bio 101, La Jolla, Calif.), then cloned by standard methods (Maniatis et al., *Molecular Cloning: A Laboratory Manual*, Cold Spring Harbor Laboratory, Cold Spring, N.Y., 1982) into pUC19 to produce pQME1 and pQME2, depending upon the orientation (FIG. 11). *E. coli* (DH5α) was then transformed with the ligation mixture by the CaCl₂ method (Davis et al., *Advanced Bacterial Genetics*, Cold Spring Harbor Laboratory, Cold Spring Harbor, N.Y., 1980). Colorless colonies of transformants that contained the insert were detected on LB with ampicillin (100 $\mu g/ml^{-1}$), isopropyl B-D-galactopyranoside (IPTG; 0.3 mM), and Bluo-gal (BRL). All recombinant DNA and vectors were harvested from *E. coli* (DH5α) by alkaline extraction (Birnboim et al., *Nucleic Acids Res.* 7:1513-1523, 1979). Plasmid DNA was separated twice from chromosomal DNA by cesium chloride (CsCl) density gradient centrifugation (Maniatis et al., *Molecular Cloning: A Laboratory Manual*, Cold Spring Harbor Laboratory, Cold Spring, N.Y., 1982). The cloned E fragment was subsequently mapped with restriction enzymes. Subfragments of the E fragment were subcloned into pUC19 for in vitro transcription/translation (IVTT). A 3.2-kb Eco RI-Hinc II subfragment was directionally cloned into pUC9 to form pQME3, and was used for in vivo expression (FIG. 12).

Gene Expression and Immunoblot Detection

A prokaryote-directed IVTT system was used as directed by the manufacturer (Amersham Corp., Chicago, Ill.) to analyze proteins coded by the E fragment, and its subcloned fragments. Translated proteins were labeled with 30 uCi [$^{35}$S]-methionine (New England Nuclear (NEN), Boston, Mass.) for 1 hour at 37° C. The approximate number of disintegrations per minute (dpm) for each IVTT sample was determined by liquid scintillation counting, as directed (Amersham). Approximately 2×10⁵ dpm per IVTT sample was boiled for 5 minutes in an equal volume of electrophoresis sample buffer (Hui et al., *J. Bacteriol.* 138:207-217, 1979), then separated by 12.5% SDS-polyacrylamide gel electrophoresis (PAGE) (Laemmli, *Nature* (London) 227:680-685, 1970). ³⁵S-labeled proteins were visualized by autoradiography following overnight exposure to X-omat X-ray film (Kodak, Rochester, N.Y.).

In vivo expression of the E protein was achieved in the SG932 strain of *E. coli*, which is defective in the degradation of abnormal proteins. A 250-μl aliquot of a fresh overnight culture of SG932 transformed with pQME3, served as the inoculum for a 5-ml LB culture containing 1 mM IPTG to induce expression. Mid-logarithmic phase cells ($OD_{600}$, ~0.6) were harvested by centrifugation and washed twice with cold 0.15N saline, then stored at −20° C. until needed. Following protein assay (Lowry et al., *J. Biol. Chem.* 193:265–275, 1951), the pellets were resuspended in SDS-PAGE sample buffer and boiled 5 minutes. Protein profiles were analyzed for expression of the E protein by immunoblot analysis (Towbin et al., *Proc. Natl. Acad. Sci. USA* 76:4350–4354, 1979). Briefly, unfixed and unstained 12.5% SDS-PAGE gels containing 30 μg protein per lane were electrotransferred to prewetted nitrocellulose (0.45 μm pore size, Schleicher and Schuell, Keene, N.H.) for 16 hours at 200 mA, with constant cooling. The filters were dried, then washed for 1 hour in phosphate-buffered saline (PBS) with 0.3% Tween 20 (v/v) and 2% nonfat milk (w/v). The filters were then exposed for 16 hours at 25° C. to rabbit anti-Priscilla OM antiserum diluted 1:1000 in PBS. Filters were washed in PBS (5X), then exposed for 1 hour to horseradish peroxidase-conjugated goat anti-rabbit immunoglobulin (Tago, Burlingame, Calif.) diluted 1:2000 in PBS. Following four washes in PBS, the filters were developed in 50 ml PBS containing O-dianisidine (0.5 $\mu g/ml^{-1}$) plus 75 ul of 30% $H_2O_2$.

DNA Sequence Determination and Analysis

The nucleotide sequence of both DNA strands of the fragment E was determined by the dideoxy chain-termination method of Sanger et al. (Sanger et al., *Proc. Natl. Acad. Sci. USA* 74:5463–5467, 1977) using $\alpha[^{32}P]dCTP$ (3,000 Ci/mmol) as the radiolabel, and commercially available reagents (Sequenase; United States Biochemical, Cleveland, Ohio). Single-stranded pGEM7 templates containing subcloned inserts of the E fragment were primed using a T7 promoter primer (Promega Biotech, Madison, Wis.). Double-stranded pGEM7 or pUC19 constructs containing E fragment subclones were primed using pUC forward or reverse primers (Promega Biotech). All double-stranded templates were purified twice by CsCl gradients. When necessary, synthetic oligonucleotide primers (17-25 mers) for sequencing of selected regions were synthesized using an Applied Biosystems DNA synthesizer (model 380A). Sequence data was complied and analyzed using CAGE/GEM (Batelle Northwest Laboratories, Richland, Wash.), the University of Wisconsin Genetics Computer Group (Deveroux et al., *Nucleic Acids Res.* 12:387–395, 1984), and Pustell (International Biotechnologies Inc., New Haven, Conn.) DNA sequence analysis programs.

DNA sequencing showed the E fragment contains an open reading frame (ORF) of 1485 bp, capable of coding for a protein of ~55.9kDa. This ORF is termed "cbE."

DNA Hybridization

Figure 13:
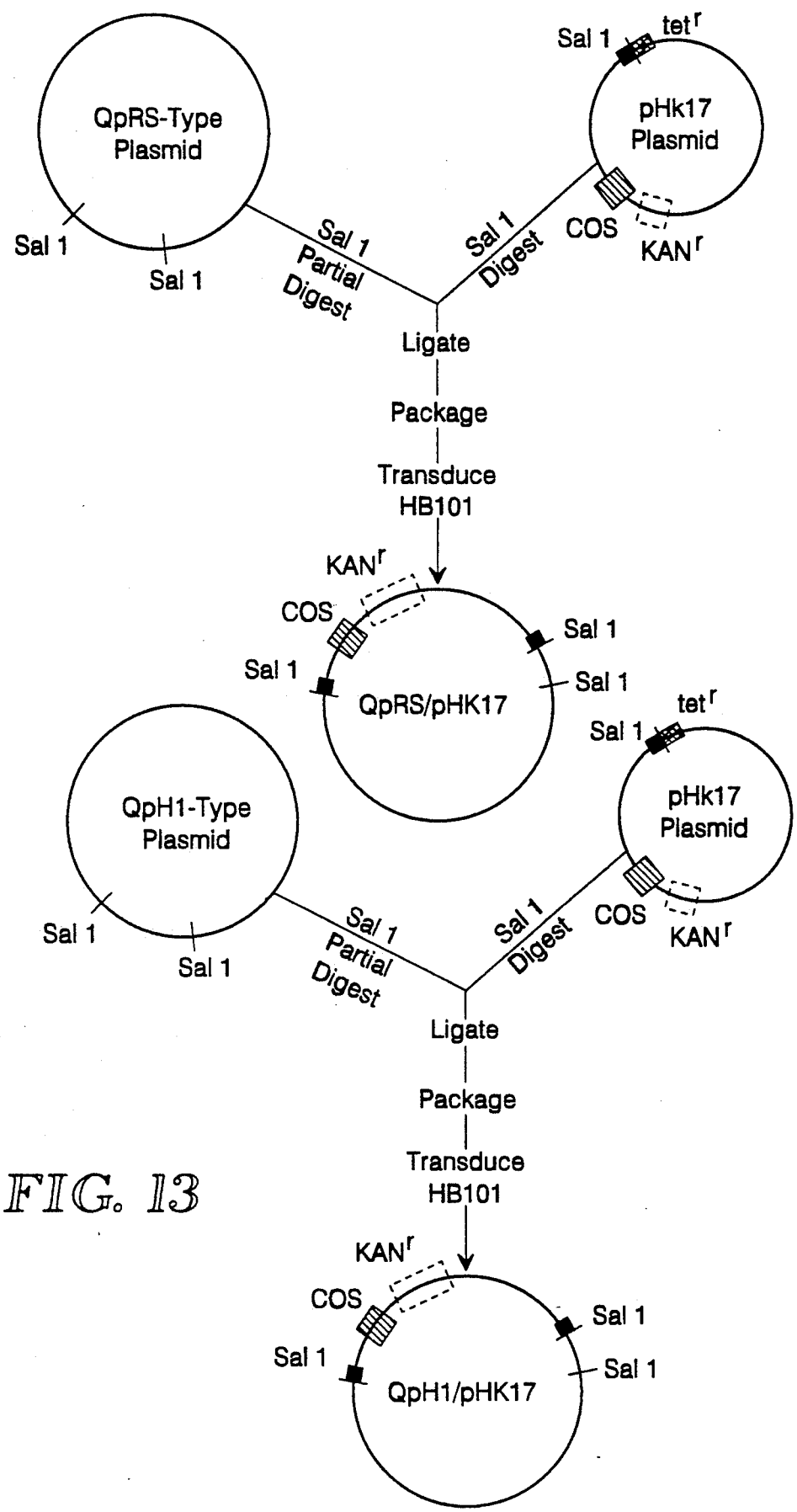
FIGS. 13a and 13b illustrate the construction of plasmids QpRS/pHK17 (i.e., pQR1) and QpH1/pHK17 (i.e., pQH1).

Southern blot analysis was used to determine the presence or absence of the cbE gene on chromosomal and/or plasmid DNA isolated from typical isolates of the four known disease-groupings of *C. burnetii*, as given above. The QpHl-type and QpRS-type plasmids, cloned in their entirety into the Sal 1 site of the cosmid vector pHK17 (Klee et al., *J. Bacteriol.* 150:327–331, 1983) to produce pQH1 and pQR1, respectively, were also probed (FIGS. 13a and 13b). The 695-bp Pst 1 fragment lying in the center of the open reading frame (ORF) of the cbE gene, as determined by sequencing, was isolated and used as a probe for the cbE gene. Briefly, the pQME1 subclone was digested to completion with Pst 1 (BRL). The 695-bp Pst 1 fragment was isolated from agarose as described above, and then labeled by random primer extension as directed by the manufacturer, using $\alpha[^{32}P]$-dCTP (NEN). Labeled DNA was purified from unincorporated isotope, using Nensorb tubes as directed (NEN). *C. burnetii* plasmid and chromosomal DNA were digested to completion with Eco RI and/or Sal 1, then electrophoresed in 1% agarose (Maniatis et al., *Molecular Cloning: A Laboratory Manual*, Cold Spring Harbor Laboratory, Cold Spring, N.Y., 1982). DNA was then transferred by the method of Southern (Southern, *J. Mol. Biol.* 98:503–517, 1975), to nitrocellulose (0.45 um pore size). The nitrocellulose was prehybridized for 1 hour at 68° C., then hybridized overnight at 68° C. with approximately $10^6$ dpm/ml of the probe. The filter was then washed at high stringency (7% mismatch), four times for 30 minutes, at 68° C. with 0.3 SSC containing 0.1% SDS and 1 mM EDTA.

Southern Blot Analysis

Figure 14:
FIG. 14 illustrates the detection of the cbE gene by Southern blot hybridization of plasmid and chromosomal DNA isolates of four known disease groupings of *C. burnetii*.

The cbE gene was detected in the restriction digests of pQME1, pQR1 and in the chromosomal DNA of the Priscilla isolate. The latter sample probably contained linearized QpRS-type plasmid contaminant from the CsCl separations. Referring to FIG. 14, detection of the cbE gene by Southern blot hybridization of plasmid and chromosomal DNA isolated from typical isolates of four known disease-groupings of *C. burnetii* is illustrated. The 695 bp Pst 1 fragment of cbE served as the probe. All DNA samples were digested with Eco RI, except lanes 2, 3, and 8, where samples are digested with Sma 1, Sal 1, and Eco RI plus Sal 1, respectively. Molecular weight standards are given in kb. Lane 1, pUC19; Lane 2, pHK17; Lane 3, pQH1; Lane 4, QpH1; Lane 5, Nine Mile chromosomal; Lane 6, pQR1; Lane 7, Priscilla chromosomal; Lane 8, pQR1; Lane 9, Dugway chromosomal; Lane 10, QpDG; Lane 11 Ko chromosomal; Lane 12, S chromosomal; Lane 13, G chromosomal; Lane 14, L chromosomal; and Lane 15, pQME1.

Expression of the cbE Gene

Figures 15A, 15B:
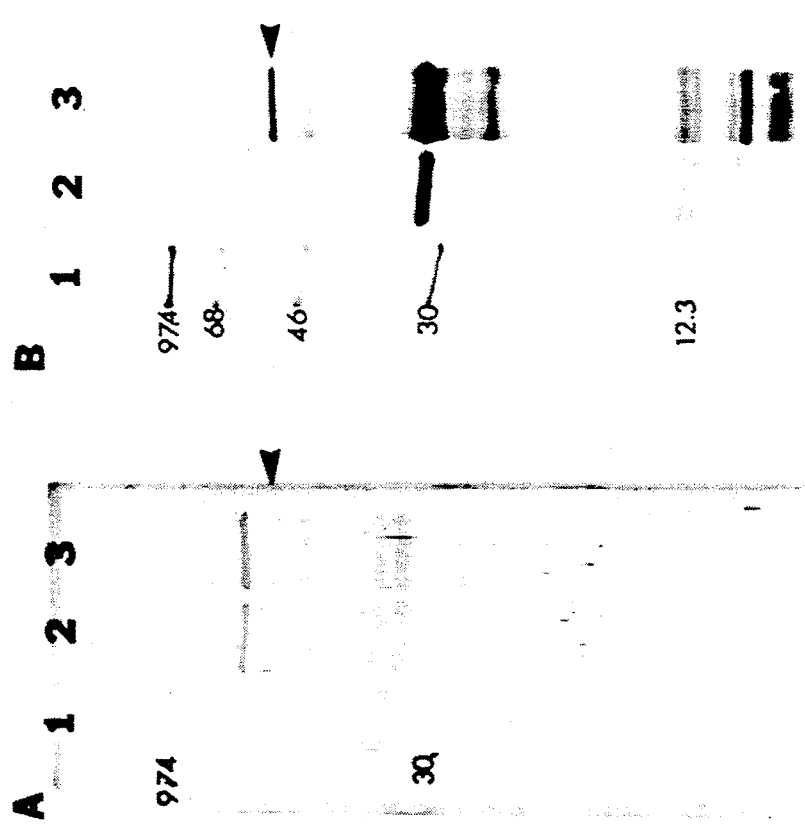
FIG. 15 illustrates the in vitro transcription/translation and immunoblot detection of the E protein of *C. burnetii* synthesized in vitro.

Referring to FIG. 15, in vitro transcription/translation (IVTT) and immunoblot detection of the E protein of *C. burnetii* synthesized in vitro is illustrated. The $[^{35}S]$-Methionine-labeled proteins were separated on 12.5% SDS-PAGE and immunoblotted, then exposed to antiserum generated against purified OM of the Priscilla isolate of *C. burnetii* (Panel A). The corresponding autoradiograph of the immunoblast is given in Panel B. In both Panel A and Panel B, lane 1 represents $^{14}C$-molecular weight standards, and lanes 2 and 3 represent IVTT products of the cloning vectors pUC19 and pQME1, respectively. The E protein is indicated by an arrowhead. Molecular weight standards are given in kDa.

Figure 16:
FIG. 16 illustrates in vivo expression of the cbE gene of *C. burnetii* in *E. coli* and immunoblast detection of the expressed E protein with rabbit antiserum generated against purified OM of the Priscilla isolate of *C. burnetii*.

On SDS-PAGE, IVTT of the pQME1 construct yielded a protein of approximately 55 kDa that was specific to the rickettsial DNA insert. A protein of same $M_r$ was produced in IVTTs of pQME2 and pQME3. The 55-kDa protein was transcribed and translated from the insert regardless of its orientation in the vector, suggesting that the gene product was transcribed from the rickettsial promoter, and that the promoter was recognized by the E. coli S30 lysate in the IVTT system. The 55-kDa protein was also detected on immunoblots of the $^{35}$S-labeled IVTT products developed with rabbit anti-Priscilla OM. The 55-kDa IVTT protein also comigrates with a radioiodinated surface protein that is specific to the Priscilla isolate. The SG932 strain of E. coli is capable of expressing the E protein in vivo. FIG. 16 illustrates the in vivo expression of the cbE gene of C. burnetii in E. coli and immunoblast detection of the expressed E protein with rabbit antiserum generated against purified OM of the Priscilla isolate of C. burnetii. In lane 1, E. coli SG932 contains the vector pUC9; and in lane 2, E. coli SG932 contains the pQME3 plasmid. Molecular weight standards are given in kDA. The detected E protein is indicated by an arrowhead. The calculated $M_r$ (~55 kDa) of the protein expressed in vivo was identical to that of the IVTT product. E. coli SG932 which contained only the cloning vector, pUC9, did not express the 55-kDa protein.

DNA Sequence Analysis of the cbE Gene

Figure 17:
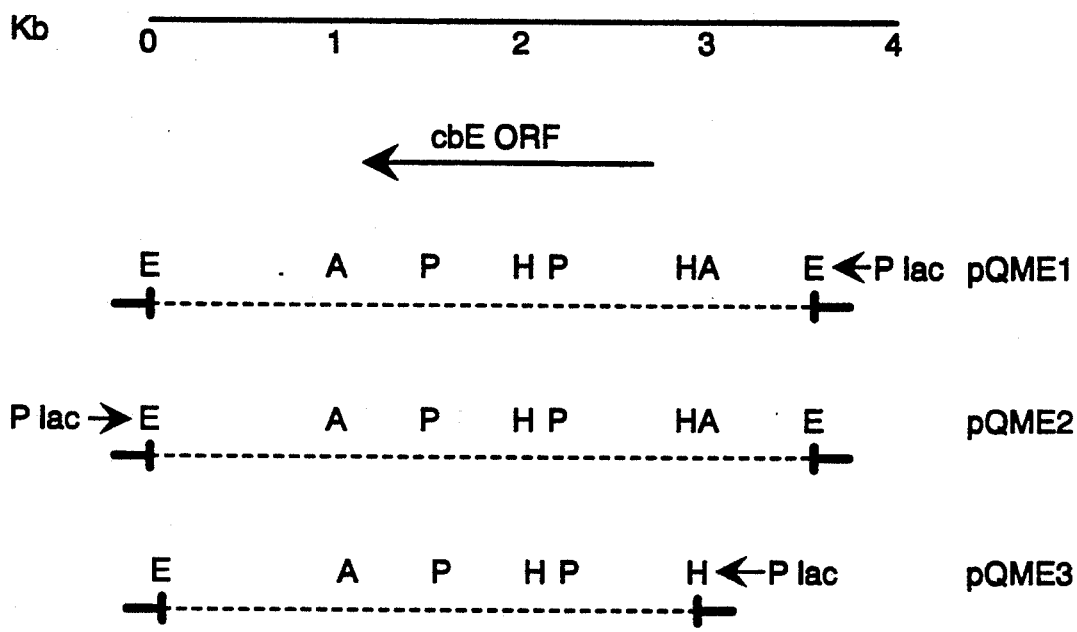
FIG. 17 depicts the open reading frame of the cbE gene and the expression thereof in plasmids pQME1, pQME2 and pQME3.

IVTT analysis of the QpRS plasmid type E fragment subclones identified a potential translation start site of the cbE gene to ca. 0.2 kb downstream of the Hinc II site located at map position 2.8 (see FIG. 17). Referring to FIG. 17, cloned DNA of the C. burnetii QpRS plasmid type was used to characterize and express the cbE gene. The rickettsial DNA insert is given as a broken line with restriction sites as indicated. (Abbreviations A, Acc 1; E, Eco RI; H, Hinc II; P, Pst 1). The large arrow designates the location and direction of the cbE ORF. The solid line represents the pUC19 vectors in the plasmids designated pQME1 and pQME2, and represents pUC9 for the plasmid pQME3. The direction of the lax promoter with respect to the insert is indicated by an arrow.

Figure 18:
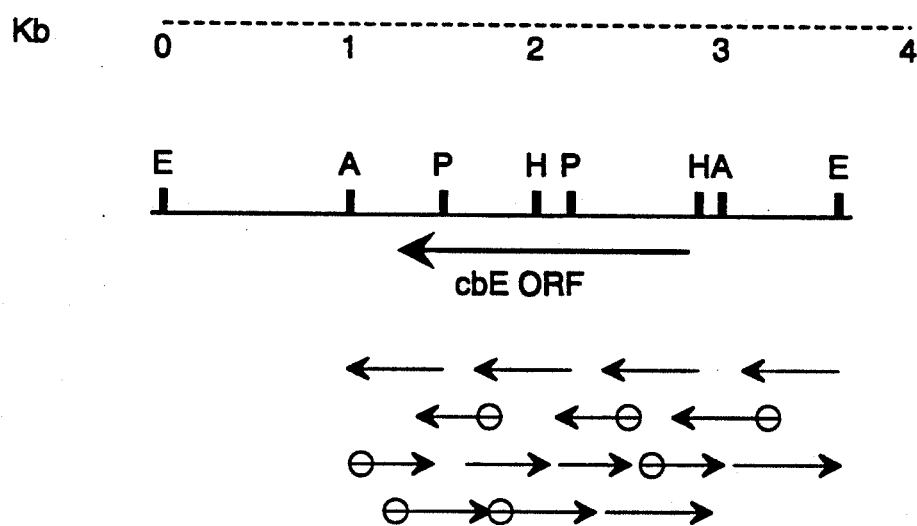
FIG. 18 depicts the sequencing strategy utilized to locate and determine the nucleotide sequence of the cbE gene.

To precisely locate the cbE gene and determine its nucleotide sequence, a portion of the E fragment was sequenced following the strategy shown in FIG. 18. The region of cloned C. burnetii QpRS-type plasmid DNA was sequenced is shown, and the sequencing strategy indicated by arrows. Plain arrows denote subcloned segments primed with commercially available primers; arrows with open circles denote segments primed internally with oligonucleotides synthesized using the deduced sequence. The large arrow designates the location and direction of the ORF of cbE. Restriction sites are indicated, (Abbreviations: A, Acc 1; E, Eco RI; H, Hinc II; P, Pst 1). An ORF long enough to code for the 55-kDa E protein was identified, starting 196 base pairs downstream from the Hinc II site at map position 2.8 and ending 293 base pairs downstream from the Pst 1 site at map position 1.7. The sequence of this 1,485 bp ORF was confirmed by sequencing both strands of DNA.

Referring to FIG. 19, the nucleotide sequence of the sense strand (5' to 3') and deduced amino acid sequence of the C. burnetii cbE gene is depicted. The nucleotide numbering begins with the Hinc II site located at coordinate 2.8 of the E fragment. Overlined are the putative −35 and −10 promoter regions of cbE. The putative Shine-Delgarno (SD) region is marked by open circles. The 3' dyads are shown by arrows. The amino acid translation is shown below the sequence, beginning at the N-terminal methionine at nucleotide 196. The boxed area represents a 12-amino acid region with hydrophobic character.

As the nucleotide sequence of FIG. 19 shows, this ORF begins with an ATG initiation codon (position 196) and ends with a TAA termination codon at position 1681, followed by a second in-frame stop codon TAG at position 1687. Beginning two bases upstream of the ATG initiation codon, the ORF of cbE is preceded by a poly-urine-rich sequence of GGAGAGA, representing a potential SD ribosomal binding sequence. This SD sequence is very similar to those found in E. coli (Gold et al., Annu. Rev. Microbiol. 35:365–407, 1981) and differs by an A-to-G transition in the first base of the sequence AGAGAGA from a SD of Rickettsia rickettsii (Anderson et al., J. Bacteriol. 169:2385–2390, 1987). In addition, a promoter-like sequence TTAAT-$N_{15}$-TATAAT existed between positions 157 and 183. The −10 region (TATAAT), which precedes the ATG initiation codon by 12 base pairs, is identical to the consensus sequence found in E. coli (Hawley et al., Nucleic Acids Res. 11:2237–2255, 1983). The −35 region of cbE differs from the E. coli consensus sequence TTGACA (Hawley et al., Nucleic Acids Res. 11:2237–2255, 1983) by substitution of the last four bases with TAAT. The cbE −35 region is more similar to the R. rickettsii −35 sequence (TTACA) that is proximal to a 17-kDa surface antigen (Anderson et al., J. Bacteriol. 169:2385–2390, 1987). The cbE −10 region TATAAT differs from this rickettsial promoter only by a C-to-A transition at base number 5.

The cbE ORF is followed by a region of dyad-symmetry with potential to act as a factor-independent terminator (see FIG. 19, nucleotide 1682 to 1732), as predicted by the "TERMINATOR" program of the University of Wisconsin's Genetics Computer Group (Deveroux et al., Nucleic Acids Res. 12:387–395, 1984). The G+C content of the sequenced coding region was 39 mole %, which compares favorably with a C. burnetii total genomic G+C content of 43 mol % (Weiss, Annu. Rev. Microbiol. 36:345–370, 1982). A distinct codon preference of U and A was observed in the first or third position of the codon (see Table 1).

TABLE 1

| \multicolumn{5}{c}{Codon usage for the cbE gene of Coxiella burnetii, and the predicted amino acid composition of the gene product.} |

| Amino Acid | No. | % of total | Codons | No. |
|---|---|---|---|---|
| Ala | 35 | 7 | GCU | 12 |
|  |  |  | GCC | 6 |
|  |  |  | GCA | 11 |
|  |  |  | GCG | 6 |
| Arg | 15 | 3 | CGU | 4 |
|  |  |  | CGC | 2 |
|  |  |  | CGA | 4 |
|  |  |  | CGG | 0 |
|  |  |  | AGA | 3 |
|  |  |  | AGG | 2 |
| Asn | 18 | 4 | AAU | 15 |
|  |  |  | AAC | 3 |
| Asp | 18 | 4 | GAU | 13 |
|  |  |  | GAC | 5 |
| Cys | 7 | 1.5 | UGU | 5 |
|  |  |  | UGC | 2 |
| Gln | 22 | 4.5 | CAA | 12 |
|  |  |  | CAG | 10 |
| Glu | 41 | 8 | GAA | 28 |
|  |  |  | GAG | 13 |
| Gly | 26 | 5 | GGU | 6 |
|  |  |  | GGC | 4 |
|  |  |  | GGA | 13 |
|  |  |  | GGG | 3 |
| His | 11 | 2 | CAU | 9 |

TABLE 1-continued

Codon usage for the cbE gene of *Coxiella burnetii*, and the predicted amino acid composition of the gene product.

| Amino Acid | No. | % of total | Codons | No. |
|---|---|---|---|---|
| | | | CAC | 2 |
| Ile | 41 | 8 | AUU | 16 |
| | | | AUC | 10 |
| | | | AUA | 15 |
| Leu | 56 | 11.5 | UUA | 15 |
| | | | UUG | 11 |
| | | | CUU | 10 |
| | | | CUC | 7 |
| | | | CUA | 9 |
| | | | CUG | 4 |
| Lys | 50 | 10 | AAA | 35 |
| | | | AAG | 15 |
| Met | 3 | 1 | AUG | 3 |
| Phe | 22 | 4.5 | UUU | 13 |
| | | | UUC | 9 |
| Pro | 22 | 4.5 | CCU | 8 |
| | | | CCC | 5 |
| | | | CCA | 4 |
| | | | CCG | 5 |
| Ser | 36 | 7 | UCU | 8 |
| | | | UCC | 8 |
| | | | UCA | 4 |
| | | | UCG | 6 |
| | | | AGU | 6 |
| | | | AGC | 4 |
| Thr | 22 | 4.5 | ACU | 5 |
| | | | ACC | 5 |
| | | | ACA | 7 |
| | | | ACG | 5 |
| Trp | 4 | 1 | UGG | 4 |
| Tyr | 20 | 4 | UAU | 14 |
| | | | UAC | 6 |
| Val | 26 | 5 | GUU | 7 |
| | | | GUC | 7 |
| | | | GUA | 7 |
| | | | GUG | 5 |

Using the nucleotide sequence and the predicted amino acid sequence of the cbE gene, a search of Genbank and NBRF data bases was conducted which revealed no significant homologies.

Features of the Predicted Amino Acid Sequence

Figure 20:
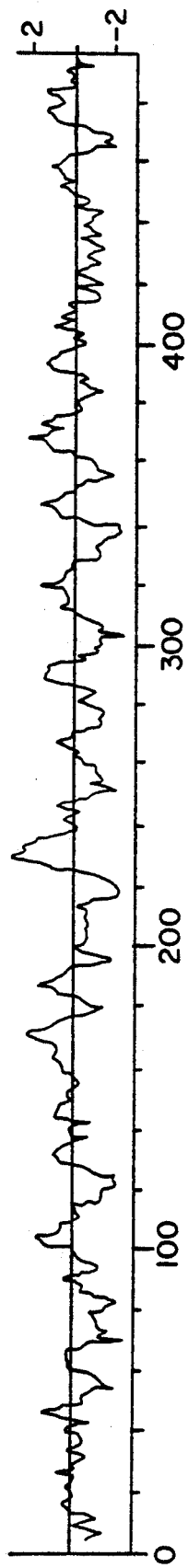
FIG. 20 depicts the hydropathy plot of the *C. burnetii* E protein.

The amino acid composition of the E protein as deduced from the nucleotide sequence is given in FIG. 19 and Table 1. The ORF of the cbE gene is capable of coding for a polypeptide of 495 amino acids with a predicted $M_r$ of 55,893 Da. This calculated molecular weight is in excellent agreement with the 55-kDa $M_r$ estimated for the E protein on SDS-PAGE. The isoelectric point of the highly charged, basic protein is predicted to be 8.7. One discrete hydrophobic domain from amino acids 224 to 235 is seen in FIG. 19, and the hydrophobicity plot (FIG. 20) indicates a possible transmembrane domain. Hydropathy was calculated by the method of Kyte and Doolittle (*J. Mol. Biol.* 157:105-132, 1982) with a span setting of nine amino acid residues. A hydrophobic segment is indicated when the plot extends into the upper half of the graph, while the lower half indicates a hydrophilic region of the protein. No hydrophobic amino-terminal signal peptide like those seen with other transmembrane polypeptides were found. (Von Heijne, *Eur.J.Biochem* 133:-17-24, 1983). Although no signal peptide was found a signal peptidase recognition site does exist at amino acids 33 to 35 (FIG. 19).

All *C. burnetti* isolates from chronic cases of the disease have contained a QpRS-type plasmid or have chromosomal DNA sequences that are homologous to a QpRS-type plasmid. Isolates from acute cases have a QpH1-type plasmid. While virulence determinants that distinguish between chronic and acute strains of *C. burnetii* are unknown, the present invention utilizes a molecular approach to determine wheather DNA sequences that are unique to the QpRS plasmid type or the QpH1 plasmid type encode for virulence determinants that are important to the chronic or to the acute manifestations of the disease.

This invention presents the first cloning and expression in *E. coil* of a plasmid-encoded gene from *C. burnetii* and the first nucleotide sequence of a Coxiella gene that is regulated by a nonheat-shock promoter. It is significant that the cbE gene is unique to a plasmid harbored by the chronic strains associated with endocarditis.

The putative surface location of the E protein is supported by data showing that antiserum generated *C. burnetii* OM can recognize the E protein on immunoblots of both IVTTs and in *E. coli* in vivo expression samples. Further evidence is the comigration of the IVT product on SDS-PAGE, with a prominently radioiodinated surface protein unique to Priscilla but absent in the Nine Mile isolate. The latter observation corroborates DNA hybridization data that cbE is present on QpRS-type plasmids from Priscilla, although it is not found in either the QpH1-type plasmid or in the chromosomal DNA of the Nine Mile isolate (see FIG. 14).

The promoter regions for the cbE gene show considerable homology to the *E. coli* consensus promoter. The SD region and Pribnow (−10) sequences are essentially identical to those found in *E. coli* (Gold et al., *Annu. Rev. Microbiol.* 35:365-407, 1981; Hawley et al., *Nucleic Acids Res.* 11:2237-2255, 1983). However, the −35 region of cbE' bears greater similarity to the −10 consensus sequence of *E. coli* and to the −35 region of a *R. rickettsii* gene (Anderson et al., *J. Bacteriol.* 169:2385-2390, 1987). The only previous report of sequenced DNA from *C. burnetii* is that of a heat shock operon composed of htpA and htpB genes. Unfortunately, the −35 and −10 regions of the htpA/htpB operon are regulated by a heat shock promoter which is not comparable to cbE regulatory regions. the htpB gene does have a SD sequence that is similar to that of cbE, while htpA apparently lacks such a sequence.

The 15-base space separating the −35 and −10 promoter sequences of cbE is marginal for recognition by *E. coli* RNA polymerase, but it is similar to that of *R. rickettsii* (Anderson et al., *J. Bacteriol.* 169:2385-2390, 1987). However, the ability of the IVTT system to recognize the Coxiella promoter and synthesize the E protein regardless of the DNA insert orientation in the vector suggests that the Coxiella promoter is recognized by the *E. coli* RNA polymerase, and that the lac promoter of the PUC vector was not responsible for transcription/translation. In vivo expression of the directionally cloned pQME3 construct in *E. coli* RNA polymerase. IPTG induction of in vivo expression was marginal, suggesting that the lac promoter played a minor role in cbE expression. In vivo expression was not achieved in *E. coli* strains that were not lon-. Analysis of cbE protein products by Maxicell analysis (Sancar et al., *J. Mol. Biol.* 148:45-62, 1981) suggested that the synthesized E protein was degraded, in spite of a number of preventative measures. Only the lon-strain SG932 provided an adequate host for accumulation of the cbE-coded protein.

The U and A nucleotide preference in codons of cbE is similar to sequenced genes of other rickettsia including the citrate synthase gene of *Rickettsia prowazekii* (Wood et al., *J. Bacteriol.* 169:3564-3572, 1987) and to the htpB gene of Coxiella (Vodkin et al., *J. Bacteriol.* 170:1227-1234, 1988). This result would be expected in an organism which has a 43 mol % G+C content (Weiss, *annu. Rev. Microbiol.* 36:345-370, 1982).

A discrete hydrophobic domain of 12 amino acids, flanked on both sides by an aspartic acid residue, was observed at approximately the center of the E protein (see FIG. 19, between amino acid residues 224 to 235). This region may represent a membrane-spanning domain of the E protein, serving to anchor it to the OM. Twelve hydrophobic amino acids have been shown to be sufficient for membrane-spanning domain (Adams et al., *Cell* 41:1007-1015, 1985). The aspartic acid residues occurring on both ends of the hydrophobic domain possibly associate with the charged heads of the OM phospholipid bilayer. However, we observed no apparent amino-terminal signal peptide with consensus to other prokaryotes (Von Heijne, *Eur. J. Biochem.* 133:17-24, 1983).

Figure 21:
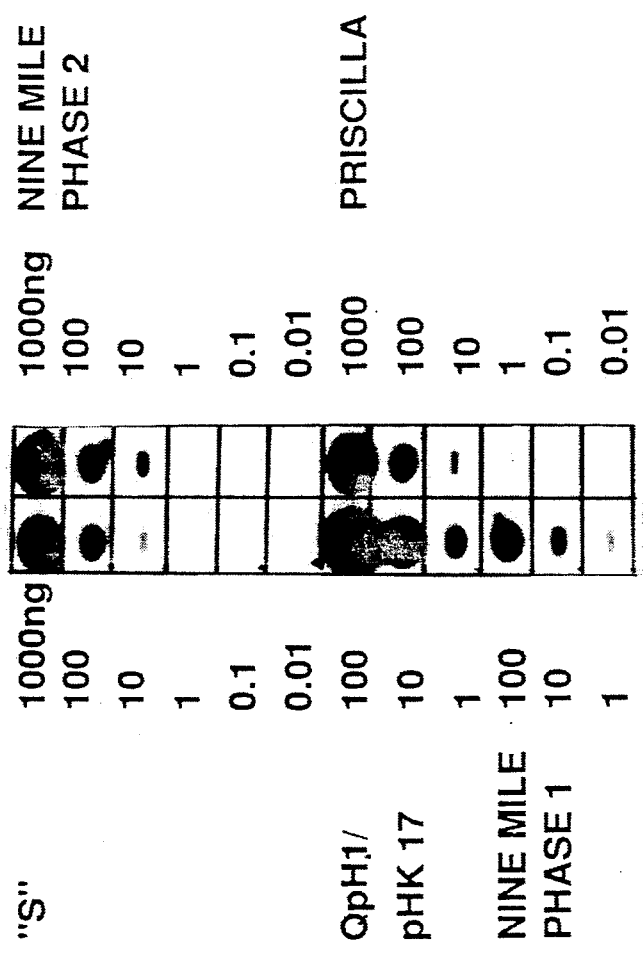
FIG. 21 illustrates the detection of both acute and chronic strains of *C. burnetii*.

Nine Mile Phase I and Nine Mile Phase II isolates of *C. burnetii* both contain a QpH1-type plasmid, the Priscilla strain contains a QpRS-type plasmid, and the "S" strain is a plasmidless strain. Referring to FIG. 21, the QpH1-type plasmid fragment from a QpH1/pHK17 hybrid plasmid (see FIG. 13) detects all three strains at sufficient DNA concentrations. The QpH1/pHK17 hybrid plasmid is included as a positive control (middle left of blot).

Figure 23:
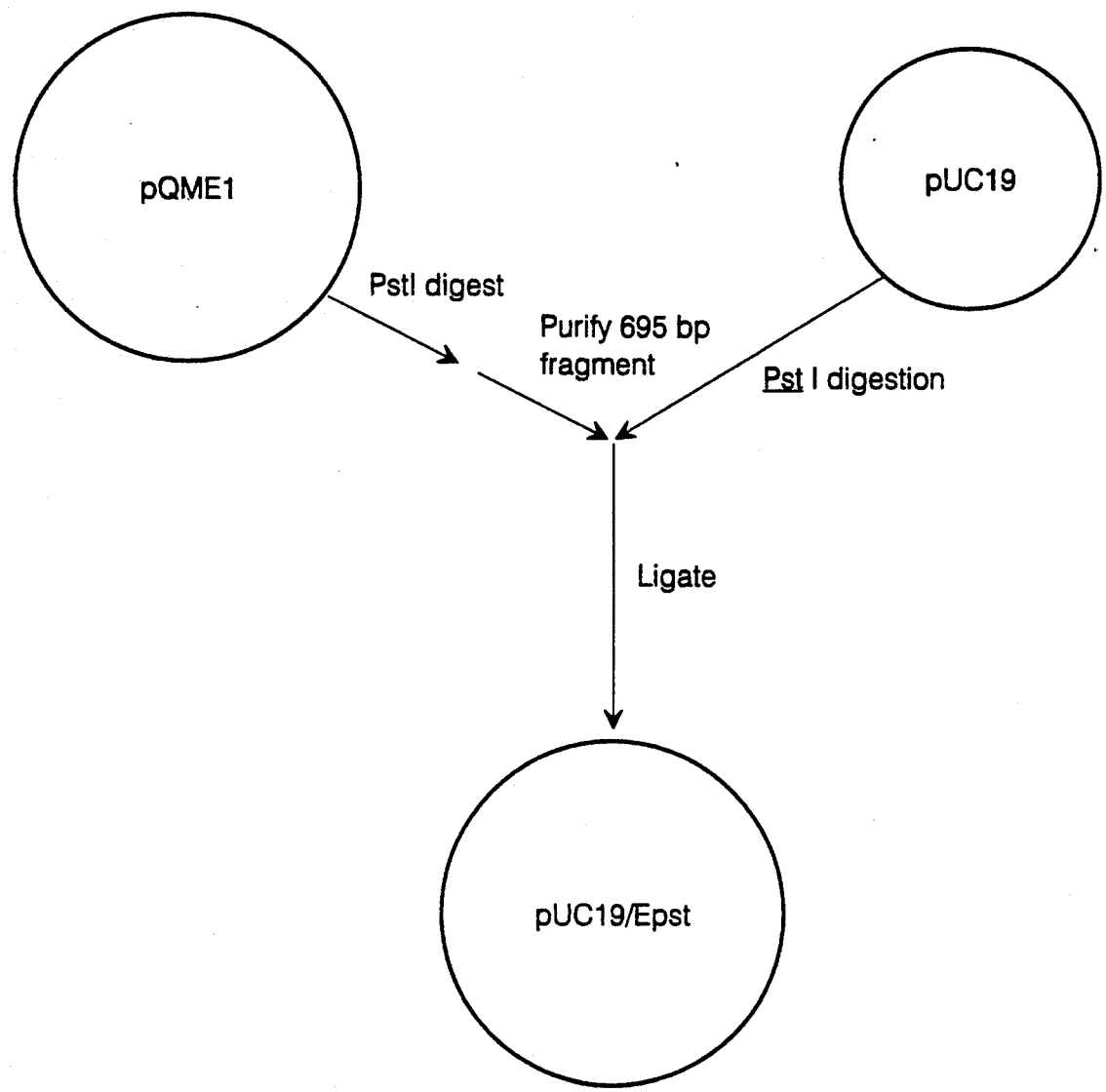
FIG. 23 illustrates the construction of plasmid pUC1-9/$E_{pst}$.

Referring to FIG. 22, the Pst fragment of E (isolated from pUC19/E$_{pst}$, see FIG. 23) detects both the chronic *C. burnetii* strains: the Priscilla strain and the plasmidless "S" strain. However, this probe does not hybridize with the acute Nine Mile Phase I and II strains which contain the QpH1-type plasmid, nor the QpH1/pHK17 hybrid plasmid. The pUC19/E$_{pst}$ hybrid plasmid is included as a positive control (bottom left of blot).

EXAMPLE IV

Genomic Grouping of *C. burnetii* Strains

DNA was analyzed from each isolate listed in Table 2. These isolates are from acute or chronic disease strains of *C. burnetii* in humans, and from a wide variety of animals and arthropods. Intact *C. burnetii* chromosomal DNA was isolated and digested to yield a convenient number of large fragments. Based upon these fragments, isolates which belong to specific genomic groups may be classified. Once the class of a particular isolate is determined, the DNA fragments may be separated electrophoretically and the appropriate bands identified by DNA/DNA hybridization, using probes derived from cloned genetically mapped genes. By this method, any isolate of *C. burnetii* may be classified by its pathogenicity, and the cellular DNA sequence thereof subsequently used to detect and/or differentiate chronic or acute strains of *C. burnetii*.

TABLE 2

Isolates of *Coxiella Burnetii*[a]

| Genomic Group | Plasmid Type | Isolate | Phase[b] | Original Source |
|---|---|---|---|---|
| I | QpH1 | 9 Mile RSA493[c] | 1 | Montana, tick, 1935 |
| | | 9 Mile RSA439 | 2 | Montana, tick, 1935 |
| | | 9 Mile RSA514 | 1 & 2 | Montana, tick, 1935 |
| | | Dyer RSA345 | 2 | USA, human blood, 1938 |
| | | American Q Dyer Strain | 2 | USA, human blood, 1938 |
| | | Australia QD RSA425 | 2 | Australia, human blood, ~1939 |
| | | Turkey RSA333 | 2 | Turkey, human blood, 1948 |
| | | African RSA334 | 1 | Central Africa, human blood, 1949 |
| | | Giroud RSA431 | 1 | Central Africa, human blood, 1949 |
| | | Ohio 314 RSA270 | 1 | Ohio, cow's milk, 1958 |
| | | Ohio 314 RSA338 | 2 | Ohio, cow's milk, 1958 |
| II | QpH1 | M-44 RSA459 | 2 | Italo-Greek, "Grita", ~1945 |
| | | M-44 Q141 | 2 | Italo-Greek, "Grita", ~1945 |
| | | Henzerling | 2 | Italy, human blood, 1945 |
| III | QpH1 | Idaho Goat Q195 | 1 | Idaho, goat, 1981 |
| | | Idaho Goat | 1 | Idaho, goat placenta, 1975 |
| | | Koka | 1 | Ethiopia, tick, 1963 |
| IV | QpRS | MSU Goat, Priscilla Q177 | 1 | Montana, goat cotyledon, 1980 |
| | | Canada Goat Q218 | 1 | Ontario, goat kid spleen, 1981 |
| | | Idaho Sheep 80-1 | 1 | Idaho, sheep liver, 1980 |
| | | K Q154 | 1 | Oregon, human heart valve, 1979 |
| | | P Q173 | 1 | California, human heart valve, 1979 |
| | | F Q228 | 1 | Washington, human heart valve, 1982 |
| | | H WSU101 | 1 | California, human heart valve, 1986 |
| V | none[d] | S Q217 | 1 | Montana, human heart valve, 1981 |
| | | L Q216 | 1 | Nova Scotia, human heart valve, 1981 |
| | | G Q212 | 1 | Nova Scotia, human heart valve, 1981 |
| | | Ko Q229 | 1 | Nova Scotia, human heart valve, 1981 |
| VI | QpDG | Dugway 7E9-12 | 1 | Utah, rodent, 1958 |
| | | Dugway 7E22-57 | 1 | Utah, rodent, 1958 |
| | | Dugway 7E65-58 | 1 | Utah, rodent, 1958 |

[a]Provided by Rocky Mountain Laboratories, National Institute of Allergy and Infectious Disease, Hamilton, MT.
[b]Determined by complement block tiltration, M. G. Peacock, Rocky Mountain Laboratories, Hamilton, MT.
[c]Reference isolates for genomic group are underlined.
[d]No plasmid detected, but plasmid-related sequences present in genomic DNA.

Resolution of DNA Fragments

Pulse field gel electrophoresis (PFGE) methods may be used to separate large DNA fragments. This technique allows the resolution of fragments of DNA as large as 10 Mb. Using PFGE coupled with digestion by restriction endonucleases allows the mapping of entire microbial genomes. Once mapped the resultant fragments can be isolated and completely characterized. In this procedure, whole *C. burnetii* cells are embedded in agarose; the cells are lysed in situ; and the resultant DNA is cut with a low-frequency restriction endonuclease. Thus, the technique of electrophoretic fractionation of intact chromosomal DNA molecules provides an alternative to classical methods for identifying genetically identical or nearly identical organisms and PFGE analysis of restriction digested *C. burnetii* DNA provides a rapid method of assigning *C. burnetii* organisms into genomic groupings and monitoring the entire genomes of these microorganisms for large chromosomal rearrangements.

Before the DNA can be fractionated, it must be liberated from cells intact and disentangled. As the size of DNA molecules increases, it becomes progressively more difficult to keep them in tact. Both mechanical shear and nucleolytic degradation must be controlled, therefore, in order to handle intact DNA molecules larger than 200 kb, it is preferable to prepare DNA samples by in situ lysis of cells within a semisolid matrix. The best results are obtained by performing cell lysis and deproteinization of *C. burnetii* DNA while the nucleic acid is immobilized in a block of agarose. The preparation of unbroken genomic DNA by embedding cells in agarose is followed by fragmentation of genomic DNA into specific large pieces by in situ digestion in agarose, high resolution size separation of the resulting DNA fragments by PFGE, and use of accurate size standards for large DNA fragments to allow sizing of the resultant fragments. The methods and the results are described in the following sections.

Intact *C. burnetii* chromosomal DNA was isolated and digested with a number of different enzymes to determine which would cut the DNA into convenient numbers of large fragments. The two restriction enzymes (Not I and Sfi I) with eight base recognition sequences gave the fewest number of DNA fragments. Not I recognizes all GC|CCGGCG sites in the DNA and Sfi I has a recognition sequence of GGCCNNNN|NGGCC.

Preparation of Gel Plugs for Restriction Endonuclease Digestion

*C. burnetii* were suspended in TE buffer (10 mM Tris-HCL, 1 mM EDTA at pH 7.5) at a concentration of $2\times10^9$ cells/ml and diluted with one volume of 1% InCert (FMC BioProducts, Rockland, Me.) low melting agarose at 37° C. The suspension was then quickly transferred to 100 μl sample holders and allowed to cool on ice for 5 min. Solidified blocks of agarose were transferred to a lysis mixture containing about 2 volumes of ES buffer (0.5M EDTA at pH 7.5 and 1% SDS). After incubation at room temperature for 30 min., proteinase K (preincubated for 2 hours) is added to 0.5 mg/ml and the mixture incubated overnight at 55° C. The blocks are washed twice in 10 vol TE for 30 min. at room temperature and then twice for one hour each at 50° C. (using five volumes of buffer to one volume of gel plugs) the blocks were stored in ES buffer at 4° C. One block, containing 3–10 μg of DNA, was used for each restriction digest.

Restriction Endonuclease Digestion of DNA

Before digestion with restriction enzymes, agarose blocks were rinsed twice for 15 min. with TE. Digestion was carried out according to manufactures (BRL, Bethesda Research Laboratories, Gaithersburg, Md.) instructions. The plugs were incubated for three hours at the appropriate temperature in a sterile 1.5 mL microfuge tube containing 500 μL of restriction buffer containing enzyme (50 U/tube) and two gel plugs. The enzyme/buffer solution is then decanted and the digestion step is repeated for a total of three incubations. The digestion is stopped by aspirating the restriction buffer and adding 1 mL of ES buffer. After incubating at 50° C. for two hours, the ES buffer is removed and 1 mL of ESP buffer (0.5M EDTA, 0.5 mg/ml proteinase K at pH 7.5 and 1% SDS) is added. The plugs are now ready for electrophoresis. The plugs can also be stored at 4° C. for up to one month.

Suggestions for Double Digestions

Sfi and Not I digestions require 100 μL/mL BSA. When multiple enzyme digestions are to be employed, they are conducted in two stages, using the enzyme with activity in the lowest salt or temperature first (Not I is incubated at 37° C. in low salt and Sfi is incubated at 50° C. high salt).

Casting the Running Gel

The casting stand and comb are rinsed with 70% EtOH just prior to use. The running gels are prepared using 1–1.5% Ultrapure Agarose (Bethesda Research Laboratories, Gaithersburg, Md.) in 0.5×TBE buffer (0.089M Tris borate, 0.089M boric acid, 0.001M EDTA at pH 8.0). The agarose is cooled to about 80° C. before pouring it into the casting stand.

Loading the Samples

After allowing the gel to cool to room temperature, the samples are loaded by placing the agar plugs (containing digested DNA from *C. burnetii*) into sterile Petri plates and slicing the gel plugs using a glass cover slip (it is important to avoid using any metal when manipulating the agar plugs). Agarose blocks are cut into two or three pieces and placed in the slots of the 0.5 cm thick, 1.0–1.5% agarose gel (up to 10 μg of DNA per lane can be used without losing resolution). Once optimal conditions are established, reproducibility is excellent. The glass cover slip can also be used to help position the plug into the gel well. In addition, pasteur pipets with tips that have been sealed, slightly bent, and alcohol-flame-sterilized, can be used to help position the plug in the well. The plug should be placed in the front and bottom of the well. It is important to avoid trapping air bubbles or mashing the agar plug while it is being positioned. Once the plugs are in place, the wells are overlayed with liquid agarose (at 55° C.) using the same running buffer and agarose concentration as the rest of the gel.

Electrophoresis

The gel is loaded into the electrophoresis unit, being careful to remove all bubbles from beneath the gel. The electrophoresis unit is filled with 2 L of 0.5×TBE buffer that has been pre-cooled to 14° C. The circulating bath is set so that it will keep the circulating buffer at about 14° C. The buffer is changed every 24 hours during long runs. The running buffer is 0.5×TBE.

Electrophoresis units from LKB (Pharmacia LKB Biotechnology, Sweden) Beckman (Beckman Instruments, Inc., Palo Alto, Calif.) or Bio Rad Laboratories (Richmond, Calif.) all worked equally well in our hand. The data of the present invention were generated by using a Bio Rad CHEF-DR Pulsed field electrophoresis apparatus.

After placing the block in the slot of a standard 1.5% agarose gel the DNA was size fractionated by PFGE. In this procedure the large DNA is stretched by the gradient field and the DNA is exposed to alternating pluses of current in two directions perpendicular to each other. The rate at which molecules orient (and therefore migrate), when the field is changed, is dependent upon the size of the molecules, at least up to 10 megabase pairs (Mb). However, the relation between DNA size and mobility during PFGE is complex. With a 45 second pulse time, mobility is nearly a linear function of size in the range between 50 and 900 kb. Gels with very short pulses (3-6 sec.) give excellent resolution for smaller fragments (between 20-50 kb). Different pulse frequencies have to be used to optimize separation of molecules in different molecular weight ranges.

PFGE separations are known to be sensitive to many experimental variables including pulse time, temperature, and electric field strength. Typical operation conditions for separation of fragments between 20 kb and 100 kb are 14° C., 1% agarose, 150 volts, with 6 second pulse times for 22 hours and 15 second pulse times for 22 hours. Pulse times of 6 seconds for 22 hours followed by a 60 second pulse for 22 hours are needed to accurately size fragments larger than 150 kb. Various pulse times can be chosen to expand portions of the molecular size range and give optimal resolution. Pulse frequencies were regulated with a Pulsewave 760 Switcher (BRL).

Staining the Gel

DNA fragment patterns are visualized after soaking the gels in 0.5 μg of ethidium bromide per ml of $H_2O$. It may be necessary to change the ethidium bromide/$H_2O$ solution twice before the gel will stain. It may also be necessary to destain the gel in $H_2O$ in order to obtain good resolution.

The gels are photographed using Polaroid 667 film with shortwave UV illumination. An exposure that often works is f4.5, the film is exposed for 25-30 seconds and developed for 40-45 seconds.

The sizes of *C. burnetii* DNA fragments can be determined by comparison with linear concatemers of bacteriophage lambda DNA (*Waterbury* and *Lane Nucleic Acids Research* 15:3930, 1987) or by comparison with the chromosomes of *S. cerevisiae* (Schwartz and Cantor, *Cell* 37:67-75, 1984). Two compression zones exist in these types of gels, one at 20-50 kb under most conditions when pulse times are greater than 6 seconds, and one above 150 kb at very short times (<20 seconds). This necessitates the running of two or more gels with different switch times in order to get a full characterization of an isolates restriction enzyme DNA fragment patterns. Since the migration of large DNA in PFGE is dependent on the sequence of the DNA, the sizes obtained with this technique are only approximate. Rather, one should look at the number and pattern of the fragments in order to differentiate between the different genomic groups. We estimate that above 400 kb, the error involved in sizing genomic fragments may be as large as 50 kb. This analysis reveals DNA fragment size polymorphisms among the different isolates which can be used to group the organisms into genomic groups.

Figure 24:
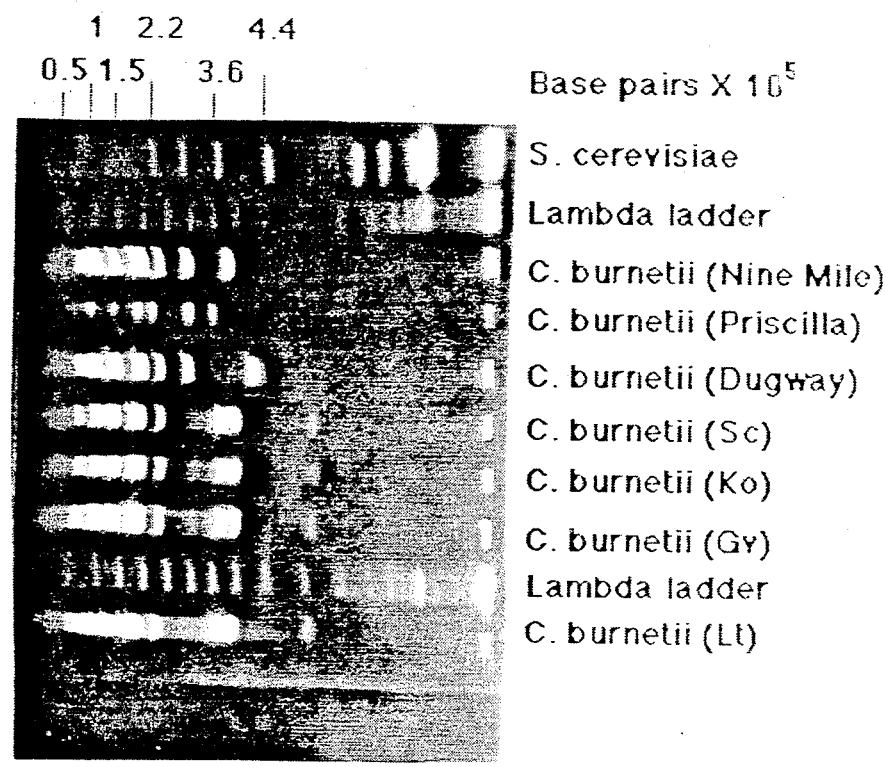
FIG. 24 depicts the classification of genomic groups I, IV, V and VI of *C. burnetii* isolates by PFGE of Not I and Sfi I digests of cellular DNA.
Figure 25:
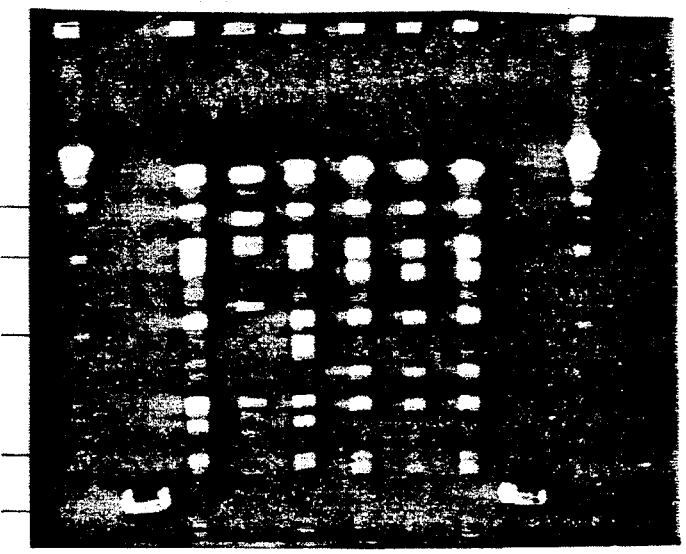
FIG. 25 depicts the classification of genomic groups II, IV, V and VI of *C. burnetii* isolates by PFGE of Not I and Sfi I digests of cellular DNA.
Figure 26:
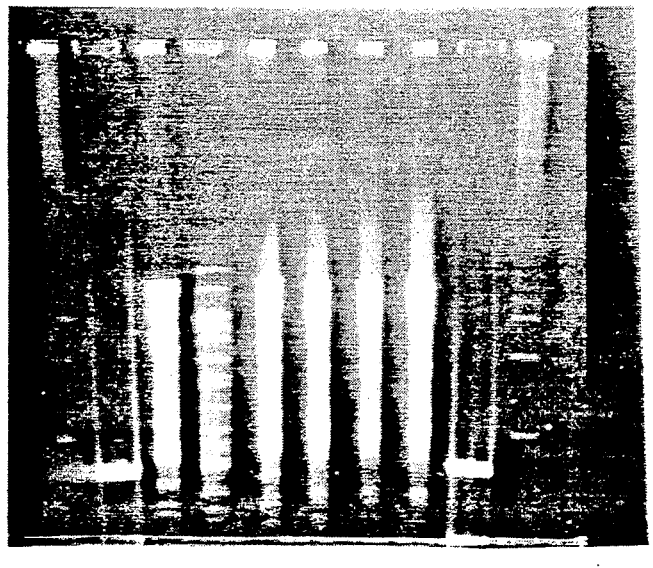
FIG. 26 depicts the classification of genomic groups III, IV, V and VI of *C. burnetii* isolates by PFGE of Not I and Sfi I digests of cellular DNA.

Sfi I and Not I restriction enzymes with eight-base recognition sequences were used to digest *C. burnetii* total cellular DNA. DNA from each of the isolates listed in Table 2 have been analyzed. These isolates are from acute or chronic disease in man, or from a wide variety of animals and arthropods. Previous studies have shown plasmid and LPS differences among isolates, which have allowed the isolates to be grouped as shown in Table 2. This grouping correlates with the pathogenic potential of the isolates, and the results of PFGE analysis illustrate that restriction enzyme digestion of total DNA can be used to identify the genomic grouping of any future related isolates. Because the technique is highly sensitive, isolates which belong to a specific genomic group have identical patterns and are easily classified. The isolates of genomic groups I, II and III have nearly identical patterns with Not I and Sfi I, but they can be distinguished by six place cutters such as Hind III or Bam H1. It should be noted that these three genomic groups also contain the QpH1-type plasmid. Representative patterns of genomic groups I, IV, V and VI after digestion with Not I or Sfi I and separation by PFGE are shown in FIGS. 24, 25 and 26. The approximate number of bands, including the size of the largest fragment, are shown in Table 3. For example, when samples of genomic group IV, *C. burnetii*, were analyzed by PFGE, 15 fragments ranging in size from 320 kbp to ~18 kbp, were observed with the Sfi I-digested DNA, and 20 fragments, including fragments from 290 kbp to ~10 kbp, were observed with the Not I-digested DNA. Summing the $M_r$ of these fragments indicates that the *C. burnetii* genome is about $1.7 \times 10^6$ bp in size, a value consistent with those obtained by renaturation kinetics.

TABLE 3

Characterization of DNA Fragments From Restriction Digestion and PFGE Analysis of *C. burnetii* Genomic Groups

| Genomic Group | DNA Restriction Fragments | | | |
|---|---|---|---|---|
| | Not 1 fragments | | Sfi I fragments | |
| | number | largest | number | largest |
| I | 19 | 250 kb | 19 | 370 kb |
| IV | 20 | 290 kb | 15 | 320 kb |
| V | 16 | 260 kb | 17 | 410 kb |
| VI | 16 | 240 kb | 16 | 380 kb |

These experiments also support the genomic groupings derived by using other procedures. A comparison of Coxiella isolates from genomic groups I, IV, V and VI reveals that because of the great heterogeneity in electrophoretic patterns of the restriction fragments among the genomic groups, it is easy to determine the genomic grouping of any new isolates.

The different strains represent diversity in both plasmid sequences and in chromosomal sequences. Specifically, each of the genomic groups have differences in the restriction endonuclease patterns in both plasmid and genomic DNA. Thus, different plasmids are not imposed on organisms with the same genomic background; rather, different plasmids are found in combination with the distinct genomic DNA sequences.

Classification of *C. burnetii* Strains

Because of the great diversity observed among *C. burnetii* isolates, it is no longer necessary to classify these organisms together. Rather, there are at least six different genomic groups of Coxiella. Designations of these groups are shown in Table 4. The Hamilton strain identifies genomic group I organisms that are represented by the Nine Mile RSA493 isolate; the Vacca strain includes genomic group II organisms that are represented by the Henzerling RSA331 isolate; Rasche is the strain designation for genomic group III organisms of the type represented by the Idaho goat Q195 isolate; the Biotzere strain includes the organisms from group IV that are represented by the Priscilla Q177 isolate; the Corazon strain denotes the "plasmidless" group V, which includes organisms represented by the S Q217 and Ko Q229 isolates; and the Dod strain contains the rodent isolates of genomic group VI.

TABLE 4

*Coxiella burnetii* Genomic Grouping, Strain Designations and Associated Plasmids

| Genomic | Strains | Plasmid Type | Size | Associated Disease |
|---|---|---|---|---|
| I | Hamilton | QpH1 | 36 kbp | Acute |
| II | Vacca | QpH1 | 36 kbp | Acute |
| III | Rasche | QpH1 | 36 kbp | Acute |
| IV | Biotzere | QpRS | 39 kbp | Chronic |
| V | Corazon | none[a] | a | Chronic |
| IV | Dod | QpDG | 51 kbp | Avirulent[b] |

[a] No plasmid detected, but plasmid-related sequences present in genome.
[b] Not virulent for guinea pigs; virulence for humans is unknown.

Probe selection and isolation involves separating the DNA fragments electrophoretically and identifying the appropriate bands by DNA/DNA hybridization, using hybridization probes derived from cloned genetically mapped genes.

Since PFGE allows the reproducible separation of restriction endonuclease digested *C. burnetii* DNA fragments into precise bands, it greatly facilitates the precise selection of large DNA fragments for cloning. Briefly, restriction endonucleases, which are specific for cutting infrequently occurring sequences, are used to create large DNA fragments which are then separated by PFGE. By blotting and hybridization, one determines the fragments containing the desired gene. This region is recovered by cutting it from the gel. The harvested band can then be cloned. As a result of this selection method, only small libraries have to be created and screened. DNA fragments as large as 1 Mb can be cloned into yeast artificial chromosomes (Burke, carle and Olson, *Science* 236:806-812, 1987).

Southern Blotting Protocol

The DNA fragments generated by these restriction enzymes that rarely cut the DNA can also be transferred to nitrocellulose and probed with known genes using standard techniques. This approach allows genetic mapping of the various Coxiella genomic groups and comparison of gene loci and genetic organization among the different genomic groups.

Transfer of DNA to Gene ScreenPlus (NEN, New England Nuclear, Boston, Mass.) was performed by the method of Southern (*J. Molecular Biology* 98:503-517, 1975). Gels are first treated for 15 minutes in 0.25M HCl. After removing the acid solution the gel is rinsed with 5×SSC (1×SSC 0.15M NaCl, 0.015M sodium citrate pH 7.0) to neutralize the solution. The gel is washed a second time with 5×SSC and placed on a rocker for 15-20 minutes, and a third time with fresh 5×SSC and agitated for at least another 15-20 minutes. Using a razor, the upper left hand corner of the gel is cut off to allow proper identification of the gel orientation. The DNA is transferred to Gene Screen Plus using the standard method. After 16-24 hours, the membrane is neutralized in 5×SSC, air dried, baked for 20 minutes at 80° C. in a vacuum oven prior to 90 seconds irradiation on a 254 nm transilluminator. The irradiation step permanently crosslinks the DNA to the filter. Probes are labeled by nick translation (Rigby et al., *J. Mol. Biol.* 113:237-251, 1977) or the random priming method (Feinberg and Vogelstein, *Anal. Biochem.* 132:6-13, 1983) and hybridization was performed at 65° C. in 3×SSC overnight. After hybridization, filters are washed successively, twice, for 15 minutes at 65° C. with 3×, 1×and 0.1×SSC. Autoradiograph exposures were made with Kodak (Rochester, N.Y.) XAR-5 film at −70° C. for 1-4 days (Antoniou, deBoer and Grovseld, *Human Genetic Disease: A Practical Approach*, Davies ed. Oxford IRL Press, Ltd,. pp. 65–84, 1989). Blots could be repeated rehybridized after an overnight 0.5M KOH incubation at room temperature.

Detection Strategy

Once it is determined that a fragment hybridizes with DNA sequences unique to either the acute or chronic strains of *C. burnetii*, or hybridizes to both the acute and chronic strains of *C. burnetii*, a detection strategy may be developed. For example, by using any two of the following probes, it is possible to detect *C. burnetii* infection and to differentiate whether the detected organisms are capable of causing chronic diease or only capable of causing acute disease.

1. Probes to detect all *C. burnetii* are prepared from DNA fragments or sequences that are present in all genomic groups of *C. burnetii*.

2. Probes to detect only those *C. burnetii* genomic groups that cause chronic disease are prepared from DNA fragments or sequences that are common to those groups, but not found in genomic groups that cause only acute disease.

3. Probes to detect only those *C. burnetii* genomic groups that cause acute disease are prepared from DNA fragments or sequences or sequences that are common to those genomic groups, but not found in genomic groups that cause chronic disease.

Figure 28:
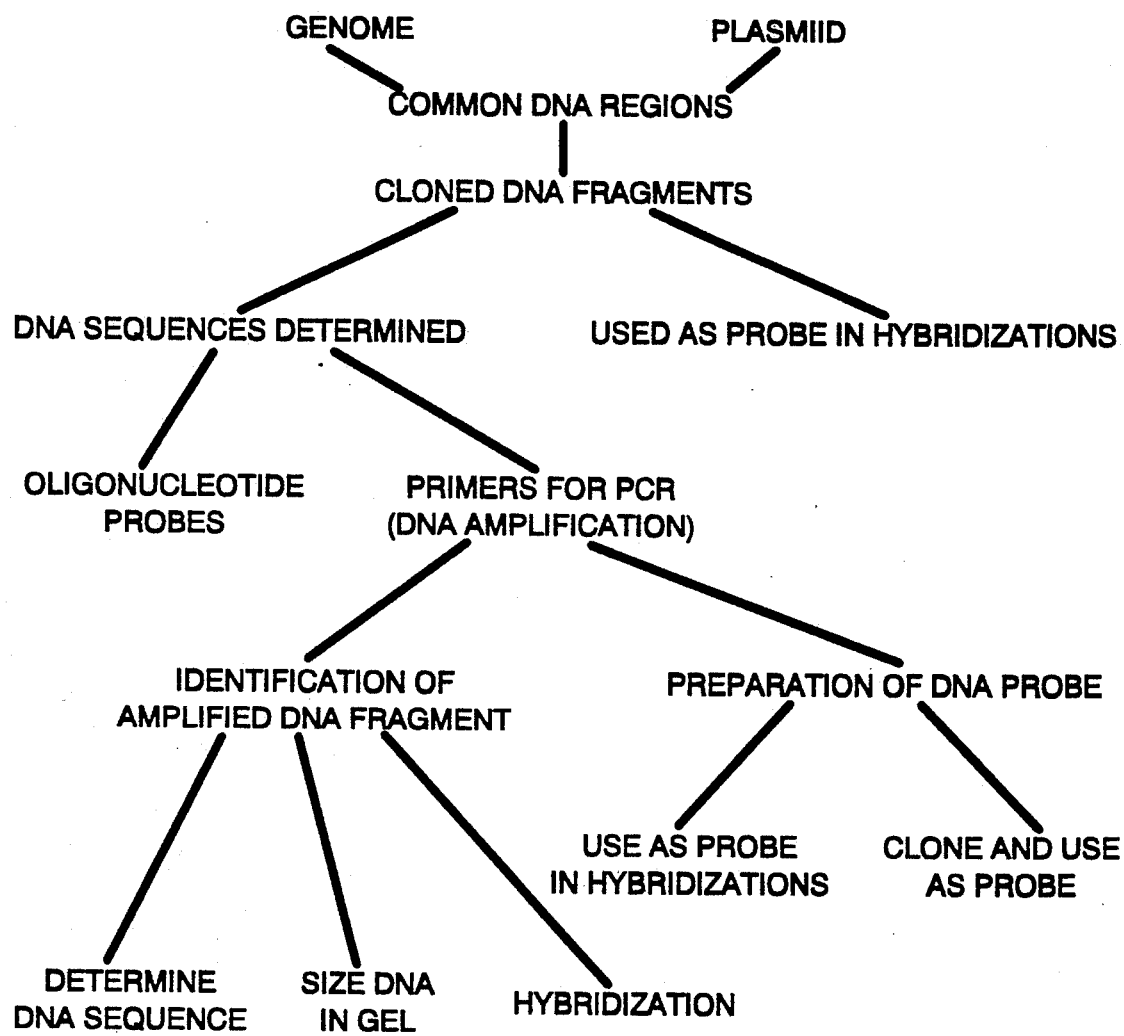
FIG. 28 illustrates a variety of techniques which may be utilized in the practice of the present invention once it is determined that a *C. burnetii* strain contains common DNA regions.

Thus, from the cellular DNA of a *C. burnetii* isolate, it may be determined by cross-hybridization whether the isolate contains regions which are shared by all *C. burnetii* strains, or are unique to either acute or chronic strains of the disease. From these common or unique regions, those skilled in the art would recognized that a number of steps may be undertaken to develop a test for the detection and/or differentiation of *C. burnetii* strains. For example, FIGS. 27 and 28 discloses a number of techniques which may be employed in the practice of the present invention.

Thus, in addition to using whole fragments or sub-fragments, primers for PCR (DNA amplification) or oligonucleotide probes may be prepared using known or derived DNA sequences. The primers or oligonucleotides may be prepared using an automated DNA synthesizer. Primers being used as probes may be end labeled (Challberg and Englund, *Meth. Enzymol.* 65:39-43, 1980) or labeled directly in the DNA synthesizer.

PCR or DNA Amplification

As previously mentioned, a method for rapid detection of *C. burnetii* and differentiation between strains that cause chronic disease and those that cause acute disease is based on the observation that the different strains contain different plasmid sequences. This method, which employs the polymerase chain reaction (PCR) for DNA amplification (Saiki et al., *Science* 230:1350-1354, 1985 and *Science* 239:487-491, 1988), requires knowledge of specific DNA sequences in the region (target) of DNA to be amplified. Two oligonucleotide primers are then prepared: one complementary to the sequence on the (+) DNA strand, and the other to a downstream sequence on the (−) strand. Thus, the primers flank the region to be amplified, so that iterative cycles of Taq I DNA polymerase chain extension are used to generate multiple copies of the DNA that lies between the two primers as discussed above. An additional technique to detect and/or differentiate acute and chronic strains of *C. burnetii* from known or derived DNA sequences is the use of oligonucleotide probes.

Nucleic Acid Detection Using Oligonucleotide Probes

The use of oligonucleotide probes in the present invention necessitates careful hybridization conditions.

Hybrids between oligonucleotides (12-25 bp) and immobilized DNA show decreased stability and an empirical formula has been determined to define the optimal conditions for their hybridization. The temperatures at which 50% of these short duplexes dissociate ($T_d$) when the hybridization is performed under standard conditions is:

$$T_d(°C.) = 4(G+C) + 2(A+T).$$

A temperature 5° C. below $T_d$ is used to detect hybridization between perfectly matched molecules. For hybrids, ≧25 pb, the Tm decreases by approximately 5° C. for every mismatched base pair. In order to minimize the hybridization of probe to related but nonidentical sequences, hybridization reactions must be performed under the most stringent conditions possible. Stringency usually can be altered by adjusting the salt and/or formamide concentrations and/or by changing the temperature. When dealing with short oligonucleotides, changing the temperature is the easiest method. The stringency can be adjusted either during the hybridization step, or in the post-hybridization washes.

The strongest signals are obtained using deproteinized nucleic acid samples since protein co-immobilization competes with the nucleic acid for binding sites on NC and also adds background. The sensitivity can be adjusted either during the hybridization step, or in the posthybridization washes.

Dextran sulfate enhances solution hybridization of large nucleotides (>250 bp) has no effect on short ones 12-50 bp.

These methods are different than those for longer probes and complex DNA:

$$T_m = 81.5° C. + 16.6 \log M + 0.41(\% G\&C) - (500/n) - 0.61(\% \text{ formamide}) - 1.5(\% \text{ mismatch})$$

The melting temperature (hybrid stability of probes longer than 50 nucleotides) is affected by ionic strength (M, in mol/liter), base composition (% G+C), the length of the shortest chain in the duplex (n), and the concentration of helix destabilizing agents such as formamide.

| Empirical Data Size of Probe | # of of A & T | $T_d$ Observed OC | 1 bp mismatch $T_d$ |
|---|---|---|---|
| 14 mer | 7 | 41 | 31 |
| 17 mer | 7 | 55 | 44 |
| 20 mer | 10 | 64 | 56 |

From the foregoing it will be appreciated that, although specific embodiments of the invention have been described herein for purposes of illustration, various modifications may be made without deviating from the spirit and scope of the invention. Accordingly, the invention is not limited except as by the appended claims.

We claim:

1. A method for detecting the presence of strains of *C. burnetii* that are capable of causing chronic disease, comprising:
    treating cells contained within a biological sample to expose cellular DNA;
    hybridizing the cellular DNA with a labeled DNA probe containing a DNA sequence that specifically hybridizes with *C. burnetii* DNA of strains associated with the capacity to cause chronic disease, wherein the DNA sequence is derived from unique sequences of a QpRS plasmid; and
    detecting the hybridized, labeled DNA probe and therefrom determining the presence of strains of *C. burnetii* capable of causing chronic disease.

2. The method of claim 1 wherein the DNA sequence of the DNA probe that specifically hybridizes with *C. burnetii* DNA associated with the capacity to cause chronic disease consists of the sequence shown in FIG. 5 or a subfragment thereof.

3. The method of claim 1 wherein the DNA sequence of the DNA probe that specifically hydridizes with *C. burnetii* DNA associated with the capacity to cause chronic disease comprises the sequence shown in FIG. 6 or a subfragment thereof.

4. A method for differentiating strains of *C. burnetii* that are capable of causing acute disease from strains that are capable of causing chronic disease, comprising:
    treating cells contained within a biological sample and suspected of containing *C. burnetii* to expose cellular DNA;
    hybridizing a first portion of the cellular DNA with a first labeled DNA probe containing a DNA sequence that specifically hybridizes with *C. burnetii* DNA;
    hybridizing a second portion of the cellular DNA with a second labeled DNA probe containing a DNA sequence that specifically hybridizes with *C. burnetii* DNA of strains associated with the capacity to cause chronic disease, wherein the DNA sequence of the second labelled probe is derived from unique sequences of a QpRS plasmid; and
    detecting the hybridized, labeled DNA probes, and therefrom differentiating the strains of *C. burnetii*.

5. The method of claim 4 wherein the DNA sequence of the second DNA probe that specifically hybridizes with *C. burnetii* DNA associated with the capacity to cause chronic disease consists of the sequence shown in FIG. 5 or a subfragment thereof.

6. The method of claim 4 wherein the DNA sequence of the second DNA probe that specifically hybridizes with *C. burnetii* DNA associated with the capacity to cause chronic disease comprises the sequence shown in FIG. 6 or a subfragment thereof.

7. The method of claim 4 wherein the DNA sequence of the first DNA probe that specifically hybridizes with *C. burnetii* DNA comprises the sequence shown in FIG. 3 or a subfragment thereof.

8. The method of claim 4 wherein the DNA sequence of the first DNA probe that specifically hybridizes with *C. burnetii* DNA comprises the sequence shown in FIG. 4 or a subfragment thereof.

* * * * *